US008845964B2

(12) United States Patent
Fukuma et al.

(10) Patent No.: US 8,845,964 B2
(45) Date of Patent: Sep. 30, 2014

(54) SAMPLE ANALYZER AND METHOD FOR CONTROLING A SAMPLE ANALYZER

(71) Applicant: Sysmex Corporation, Kobe (JP)

(72) Inventors: Daigo Fukuma, Kobe (JP); Keisuke Kuwano, Kobe (JP)

(73) Assignee: Sysmex Corporation (JP)

(*) Notice: Subject to any disclaimer, the term of this patent is extended or adjusted under 35 U.S.C. 154(b) by 38 days.

(21) Appl. No.: 13/626,257

(22) Filed: Sep. 25, 2012

(65) Prior Publication Data
US 2013/0079921 A1    Mar. 28, 2013

(30) Foreign Application Priority Data

Sep. 27, 2011  (JP) ................. 2011-211147

(51) Int. Cl.
G01N 33/00 (2006.01)
G01N 21/00 (2006.01)
G01N 35/10 (2006.01)
G01N 35/02 (2006.01)
G01N 35/00 (2006.01)
G01N 33/48 (2006.01)

(52) U.S. Cl.
CPC ........ G01N 35/0092 (2013.01); G01N 35/1004 (2013.01); G01N 35/026 (2013.01); G01N 2035/0094 (2013.01); G01N 35/00 (2013.01)
USPC ................. 422/67; 422/68.1; 422/73; 422/64

(58) Field of Classification Search
CPC  G01N 35/026; G01N 35/00663; G01N 35/02
USPC .......................................................... 422/67
See application file for complete search history.

(56) References Cited

U.S. PATENT DOCUMENTS

| 4,451,433 | A | * | 5/1984 | Yamashita et al. ............... 422/63 |
| 5,902,548 | A | * | 5/1999 | Watts et al. ...................... 422/64 |
| 2002/0110917 | A1 | * | 8/2002 | Matsubara et al. .............. 436/46 |
| 2004/0105783 | A1 | * | 6/2004 | Yamazaki et al. ............... 422/64 |
| 2004/0253146 | A1 | * | 12/2004 | Shiba et al. ..................... 422/64 |
| 2005/0207938 | A1 | * | 9/2005 | Hanawa et al. .................. 422/64 |
| 2006/0165562 | A1 | * | 7/2006 | Matsubara et al. ............ 422/100 |
| 2007/0048868 | A1 | * | 3/2007 | Shibata et al. .................. 436/43 |
| 2008/0003137 | A1 | * | 1/2008 | Burkhardt et al. .............. 422/64 |
| 2008/0050279 | A1 | * | 2/2008 | Fujita ............................. 422/67 |
| 2010/0104478 | A1 | * | 4/2010 | Kondou ........................ 422/100 |
| 2010/0108101 | A1 |   | 5/2010 | Shibata et al. |

FOREIGN PATENT DOCUMENTS

JP    2003-254980 A    9/2003

* cited by examiner

Primary Examiner — Jill Warden
Assistant Examiner — Brittany Fisher
(74) Attorney, Agent, or Firm — Brinks Gilson & Lione

(57) ABSTRACT

A sample analyzer comprising: a measurement section; a transportation section; an identification data obtainer; and a system controller; is disclosed. The system controller is configured to acquire a result of determination regarding whether a sample needs a re-measurement for a sample based on a result of a measurement of the sample. When the system controller recognizes a presence of the washing fluid tube transported by the transportation section before a determination result regarding a necessity of re-measurement is obtained for an already aspirated sample, the system controller prohibits the supply of the washing fluid in the washing fluid tube to the measurement section.

17 Claims, 20 Drawing Sheets

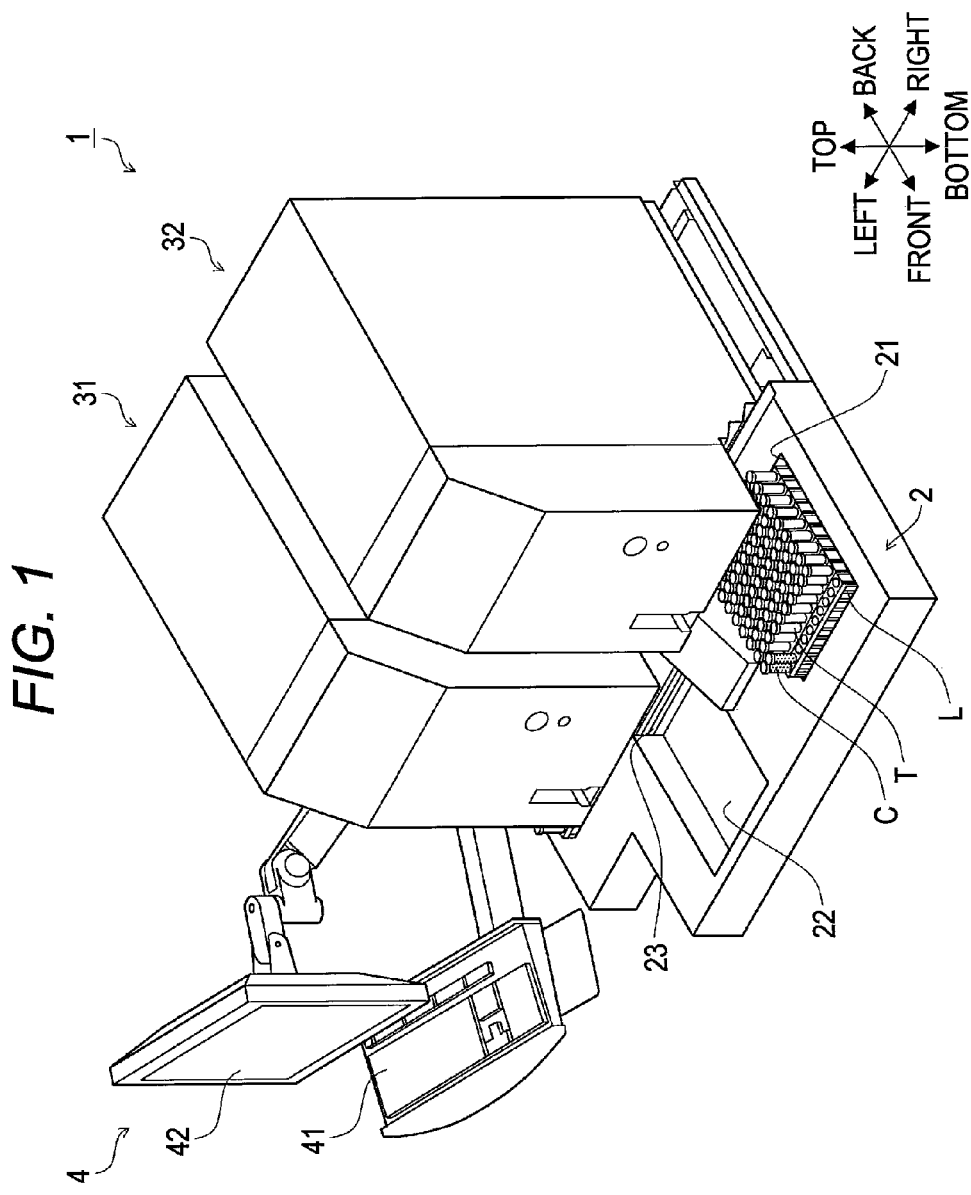

DOWNSTREAM ← → UPSTREAM

: WASHING FLUID TUBE
: SAMPLE TUBE
: NO TUBE

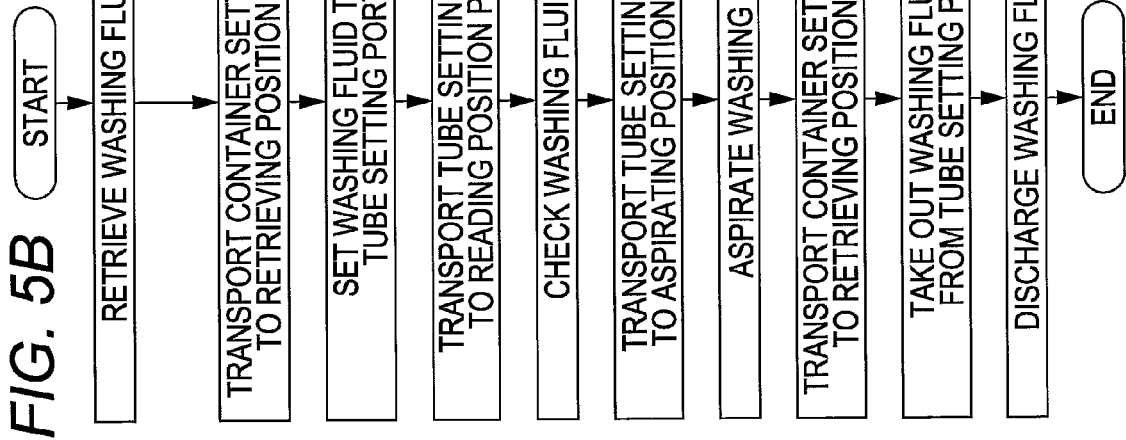
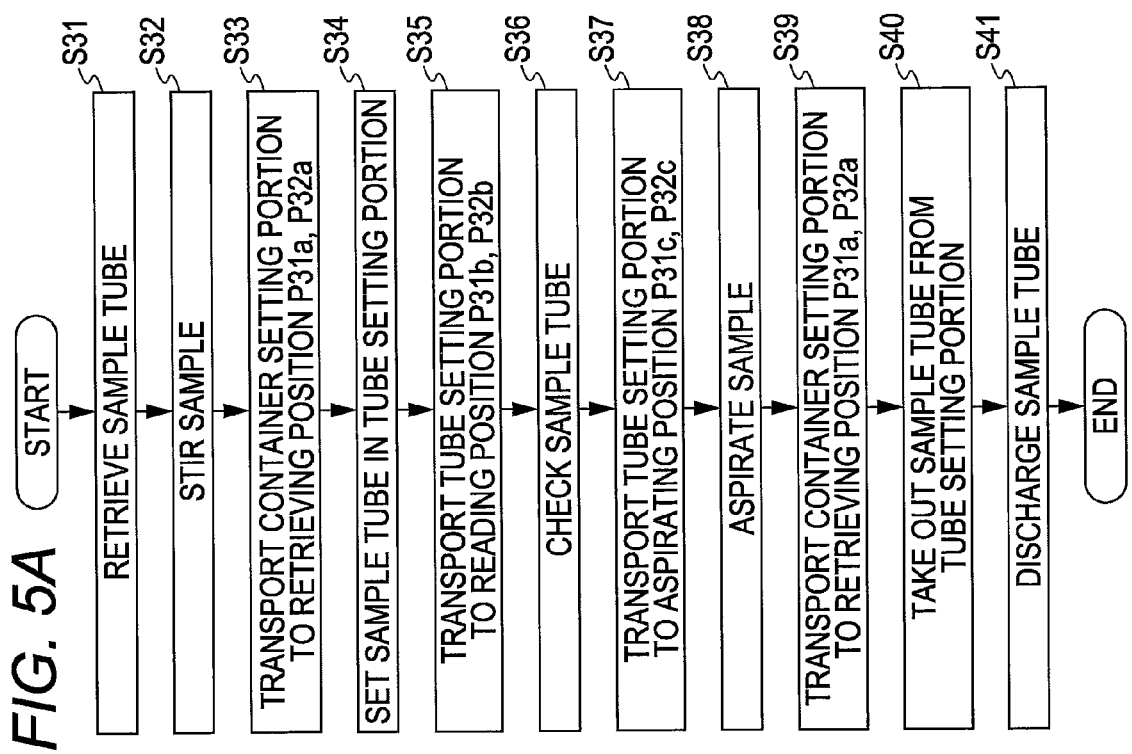

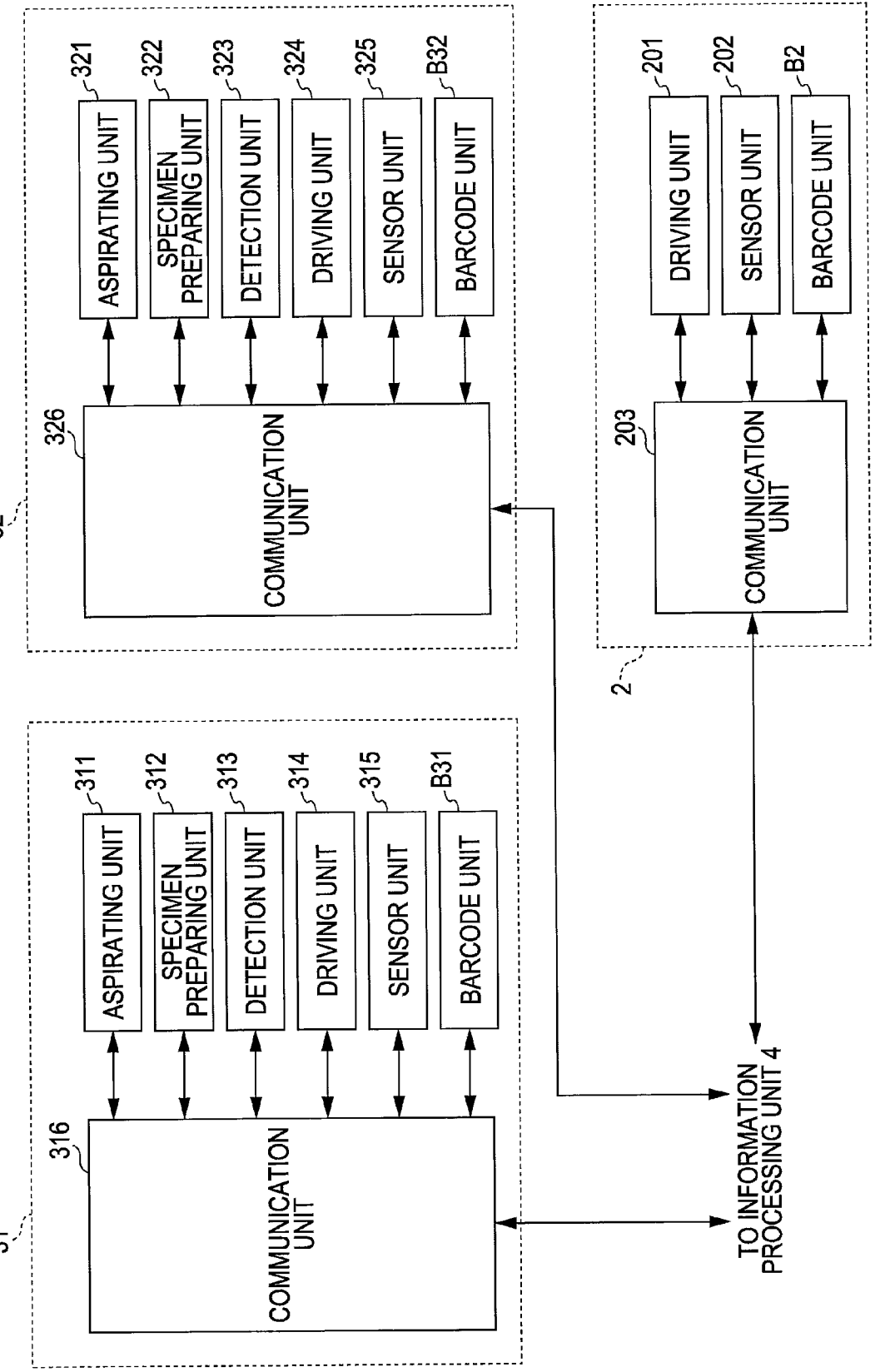

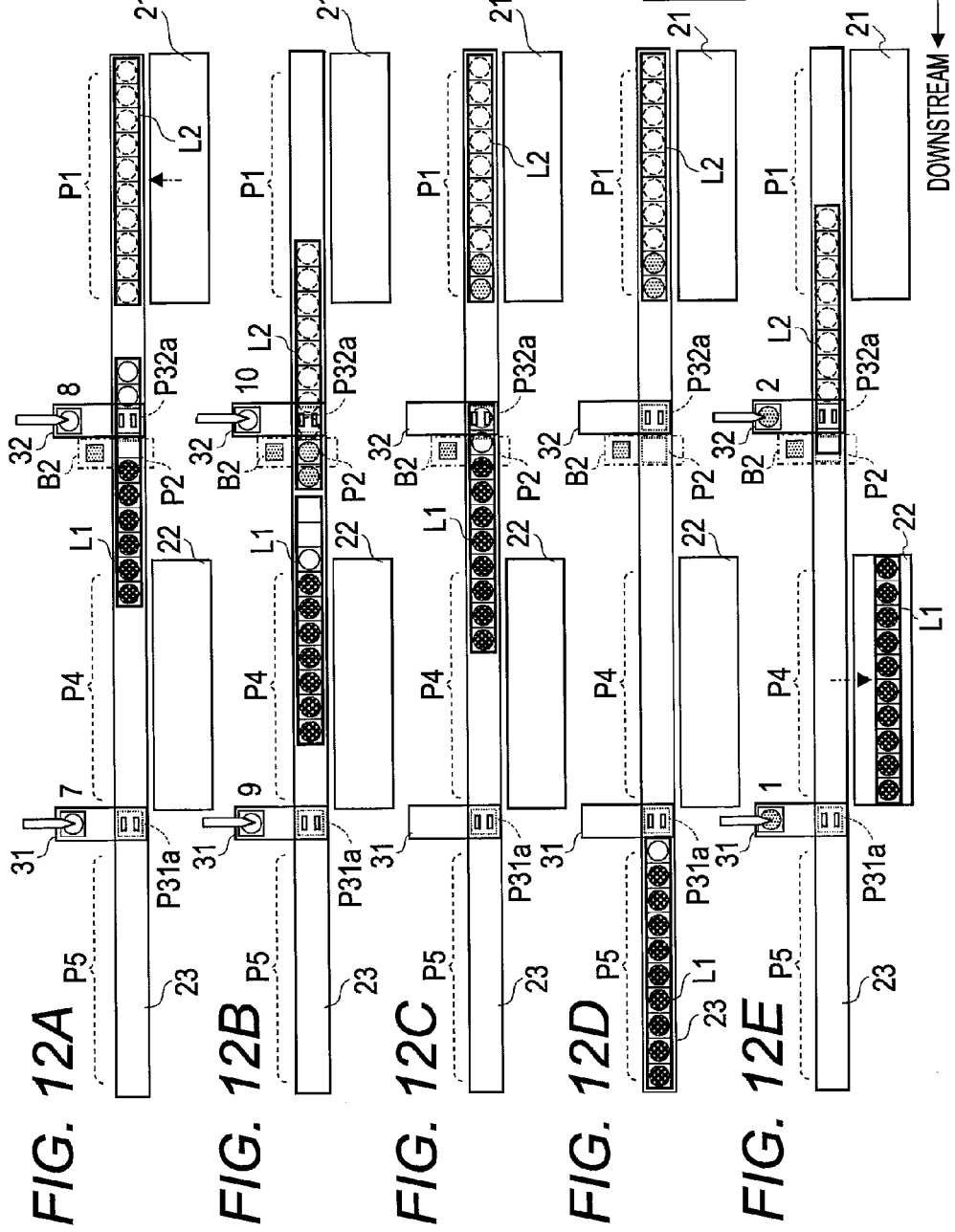

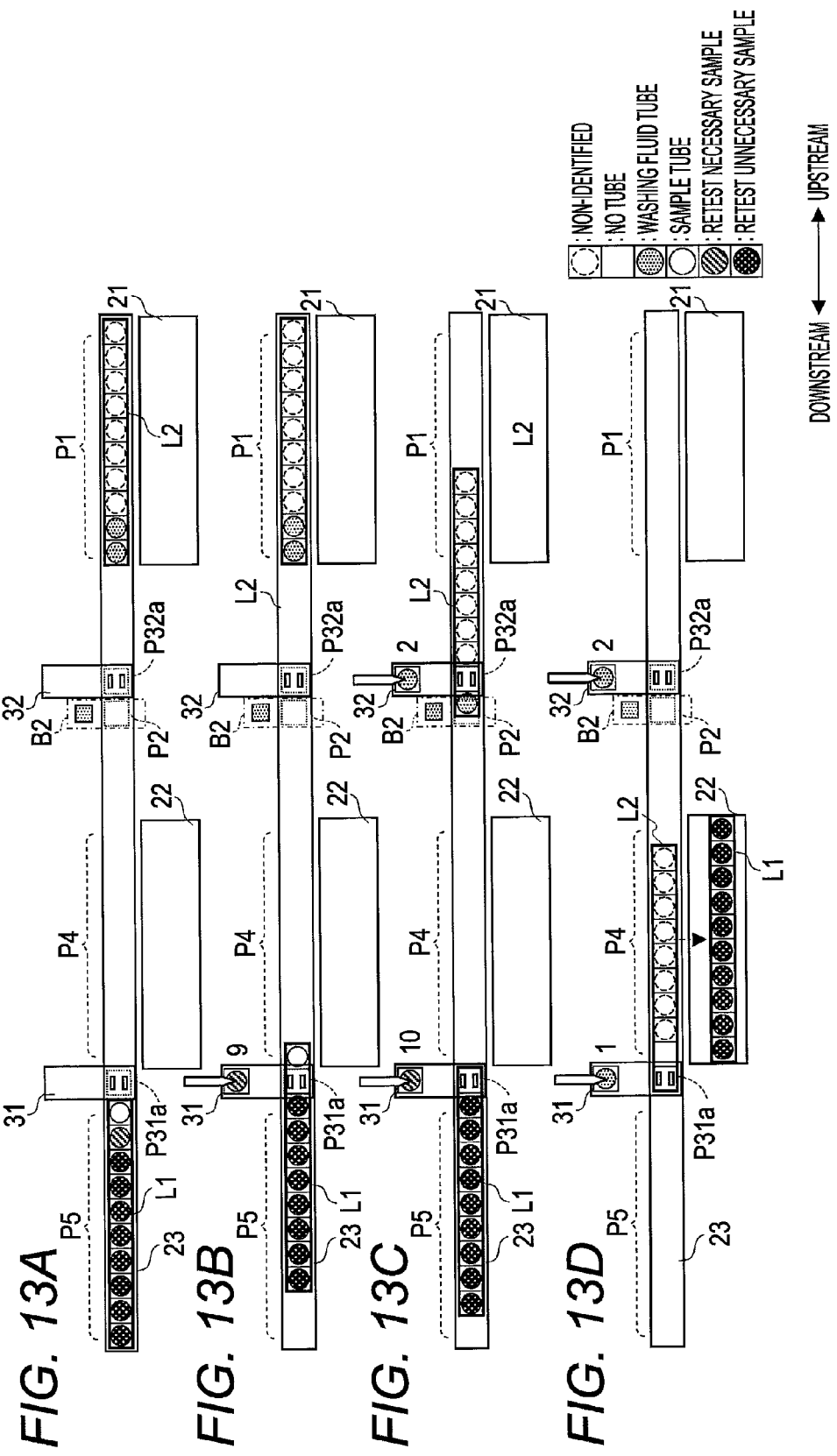

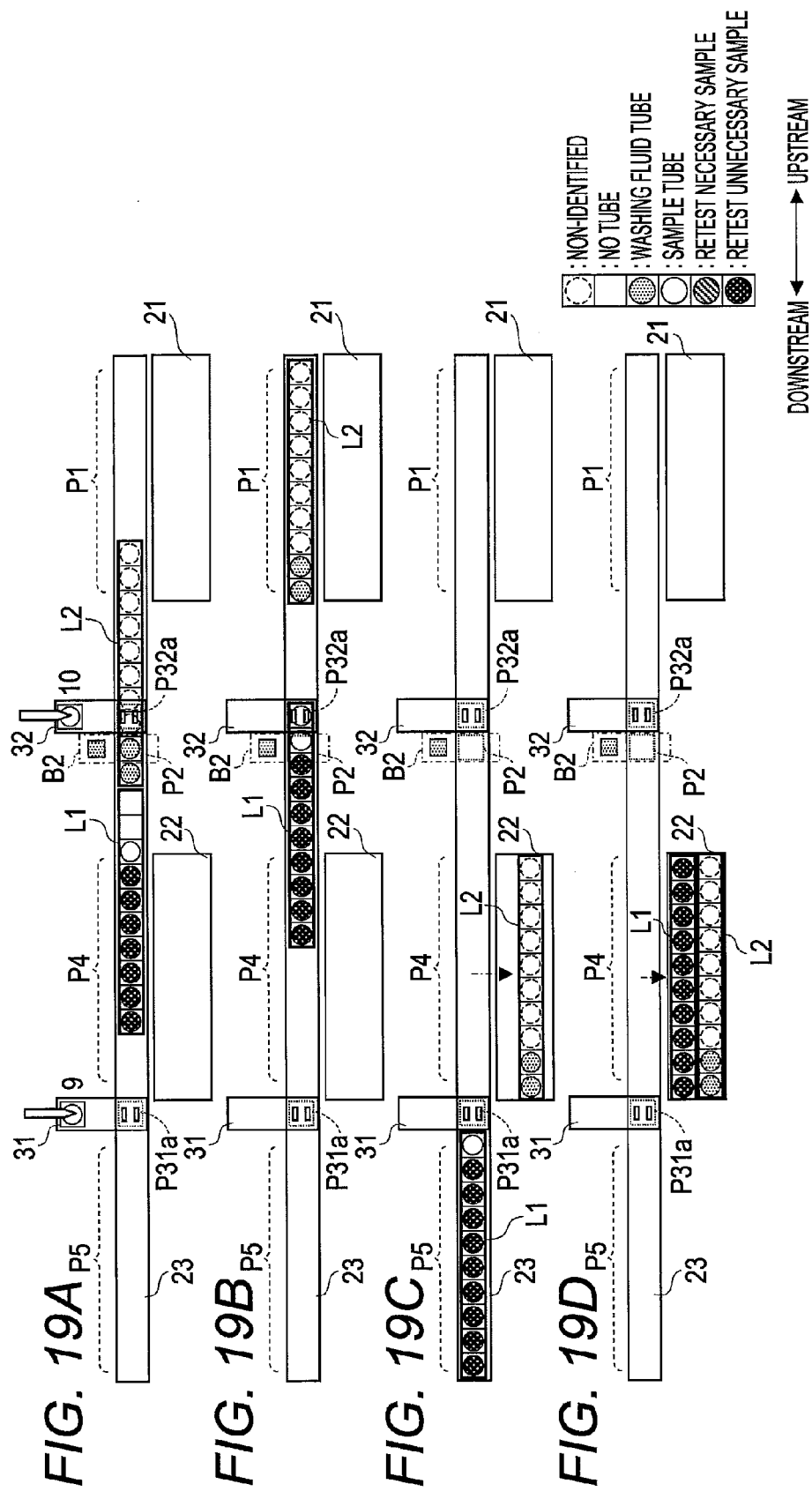

SAMPLE ANALYZER AND METHOD FOR CONTROLING A SAMPLE ANALYZER

RELATED APPLICATIONS

This application claims priority under 35 U.S.C. §119 to Japanese Patent Application No. 2011-211147 filed on Sep. 27, 2011, the entire content of which is hereby incorporated by reference.

BACKGROUND OF THE INVENTION

The present invention relates to a sample analyzer for analyzing a clinical sample such as blood, urine or the like. The present invention also relates to a method for controlling such a sample analyzer.

A sample processing apparatus for aspirating a sample through an aspirating tube from a sample tube containing samples such as blood, urine or the like, and processing the sample is known.

If the sample processing apparatus is used for a long time, dirt may be accumulated in a fluid system such as aspiration tube, flow path, valve, reaction tube, and analyzing section. This may cause a lowering of the accuracy or cause operation failure. Thus the fluid system needs to be periodically washed for every predetermined time period or for every predetermined number of tests.

Japanese Laid-Open Patent Application No. 2003-254980 discloses a specimen analyzer featured in an automatic washing. The apparatus is capable of aspirating a washing fluid contained in a fluid tube through an aspirating section, and washing an interior fluid circuit. With such configuration, when a rack holding the washing fluid tube is set in the specimen analyzer, the set rack is transported. The washing fluid is automatically aspirated from the washing fluid tube and the fluid circuit is washed when the apparatus recognizes that the transported tube on the rack is washing fluid tube.

The washing of the fluid circuit using the washing fluid is carried out by filling the chamber used to prepare a measurement specimen, the detection unit, and the flow path for connecting the same with the washing fluid and leaving it untouched for a certain time, and thereby causing the dirt deposited inside the chamber and the flow path to be solved into the washing fluid. Therefore, a long time is required to perform a washing once. Accordingly, the sample cannot be measured for a long time once the washing is started. The washing using the washing fluid is thus preferably performed after all the measurements of the sample are finished.

However, some samples require to be subject to re-measurement after the initial measurement. The determination on whether or not re-measurement is necessary is not made immediately after the completion of initial measurement, that is, there is a time lag between the time when the initial measurement is finished and the time when the determination is completed.

Thus, there may be such a case where it is determined that a sample requires to be re-measured by a measurement apparatus, after that the measurement apparatus finished an aspiration of washing fluid from a washing fluid tube, In this case, the re-measurement of the sample needs to wait for a long time until the washing is finished.

SUMMARY OF THE INVENTION

A first aspect of the present invention is a sample analyzer comprising: a measurement section configured to aspirate a sample in a sample tube and measure the aspirated sample; a transportation section configured to transport a plurality of tubes for supplying the tubes to the measurement section; an identification data obtainer configured to obtain identification data of the tube transported by the transportation section; and a system controller; wherein the system controller is configured to: acquire a result of determination regarding whether a sample needs a re-measurement, the determination being made based on a result of a measurement of the sample; when recognizing a presence of a washing fluid tube transported by the transportation section based on the identification data obtained by the identification data obtainer, control the transportation section to supply the washing fluid tube to the measuring section, and control the measurement section to aspirate the washing fluid from the washing fluid tube and then to use the aspirated washing fluid to wash at least one part of the measurement section; and when a presence of the washing fluid tube transported by the transportation section is recognized before the determination result is obtained for the already aspirated sample, prohibit the supply of the washing fluid in the washing fluid tube to the measurement section.

A second aspect of the present invention is a sample analyzer comprising: a measurement section configured to aspirate a sample in a sample tube and measure the aspirated sample, a transportation section configured to transport a plurality of tubes to supply the tubes to the measurement section; and a system controller, wherein the system controller acquires a determination result regarding whether a sample needs a re-measurement, the determination being made based on a result of a measurement on the sample; the measurement section aspirates washing fluid in a washing fluid tube and then uses the aspirated washing fluid to wash at least one part of the measurement section if the washing fluid tube is supplied by the transportation section; and the sample analyzer retains the supply of the washing fluid in the washing fluid tube to the measurement section if the washing fluid tube follows the sample tube in an order of supplying the tubes to the measurement section until the system controller completes acquisition of the determination result of the sample in the preceding sample tube.

A third aspect of the present invention is a method of controlling a sample analyzer comprising the steps of: (a) transporting a tube to a first position; (b) acquiring identification data from the tube at the first position, and determining whether the tube is a sample tube or a washing fluid tube; (c) transporting the tube to a second position for supplying the tube to a measurement section if the tube is determined as the sample tube in the determination of the step (b); (d) determining whether determination regarding a necessity of re-measurement is completed for a sample already aspirated by the measurement section, if the tube is determined as the washing fluid tube in the determination of the step (b); (e) transporting the washing fluid tube to the second position and controlling the measurement section to use the washing fluid in the washing fluid tube to executing a washing if the determination is completed in the determination of the step (d); and (f) prohibiting the execution of (e) if the determination is not completed in the determination of the step (e).

BRIEF DESCRIPTION OF THE DRAWINGS

FIG. 1 is a perspective view showing an external appearance of a sample analyzer according to an embodiment;

FIG. 5A is a view showing a flowchart of a retrieving operation of the sample tube according to the embodiment; and FIG. 5B is a view showing a flowchart of a retrieving operation of the washing fluid tube according to the embodiment;

FIG. 6 is a view showing an outline of a configuration of the transportation unit and the measurement unit according to the embodiment;

FIG. 12A-12E are views showing a flow of an operation of a rack according to the embodiment;

FIG. 13A-13D are views showing a flow of an operation of a rack according to the embodiment;

FIG. 19A-19D are views showing a flow of an operation of a rack according to the modified embodiment 4.

DETAILED DESCRIPTION OF THE PREFERRED EMBODIMENTS

Figure 2A:
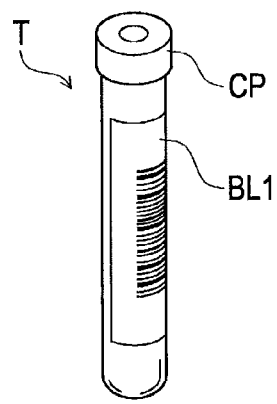
FIG. 2A is a view showing a configuration of a sample tube according to the embodiment.

The present embodiment applies the present invention to a sample analyzer for performing tests and analysis on blood.

The sample analyzer according to the present embodiment will be hereinafter described with reference to the drawings.

FIG. 1 is a perspective view showing an external appearance of a sample processing apparatus 1. The sample processing apparatus 1 according to the present embodiment is mainly composed of a transportation unit 2, two measurement units 31, 32 each including a blood cell counting section, and an information processing unit 4 (system controller).

The transportation unit 2 is arranged on a front side of the measurement units 31, 32. The transportation unit 2 includes a right table 21, a left table 22, and a rack transporting portion 23 connecting the right table 21 and the left table 22. The right table 21 and the left table 22 can accommodate a plurality of racks L capable of holding ten tubes (sample tubes T or washing fluid tubes C).

The transportation unit 2 can accommodate the rack L that has been placed by a user on the right table 21. The transportation unit 2 transports the rack L accommodated in the right table 21, and positions the rack L at a predetermined position of the rack transporting portion 23 so that the sample tube T and the washing fluid tube C on the rack L are supplied to the measurement units 31, 32. Furthermore, the transportation unit 2 transports the rack L on the rack transporting portion 23 to the left table 22. Thus, the rack L is transported along a flow from the right table 21 towards the left table 22. Hereinafter, a direction of approaching the right table 21 is referred to as "upstream of transporting direction", and a direction of approaching the left table 22 is referred to as "downstream of transporting direction" in the transportation path.

In the present embodiment, the tube accommodated in the rack L is retrieved and processed by the measurement units 31, 32 in order from the downstream of the transporting direction at a retrieving position P31a or P32a (see FIG. 4) on the rack transporting portion 23.

Figure 2B:
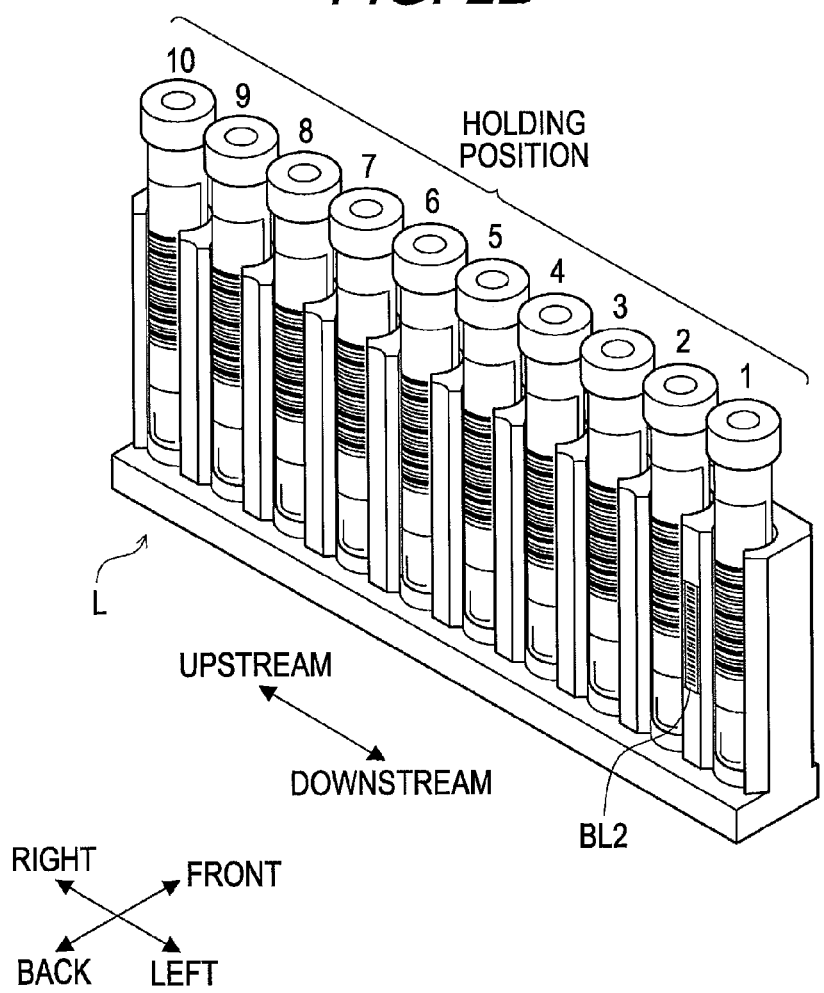
FIG. 2B is a view showing a configuration of a rack according to the embodiment.

FIG. 2A is a perspective view showing an external appearance of the sample tube T, and FIG. 2B is a perspective view showing an external appearance of the rack L holding ten sample tubes T. In FIG. 2B, the direction (front-back, left-right and upstream-downstream of transporting direction of FIG. 1) of when the rack L is mounted on the transportation unit 2 is also shown.

With reference to FIG. 2A, the sample tube T is a tube having a bottom and being made of glass or synthetic resin having translucency, and has an upper end opened. The blood sample of the whole blood collected from patient is accommodated inside, where the opening at the upper end is sealed by a lid CP made of rubber. In this embodiment, as the sample tube T having such configurations, a vacuumed blood collection tube is shown. A barcode label BL1 is attached to the side surface of the sample tube T. A barcode including a sample ID is printed on the barcode label BL1.

With reference to FIG. 2B, ten holders are formed in the rack L at holding positions 1 to 10. As shown in the FIG. 2B, ten sample tubes T can be held lined in a perpendicular state (upright state). In order to explain easily, serial numbers are assigned for the respective holding positions from the downstream to the upstream of the transporting direction.

A barcode label BL2 is also attached to a side surface on the back side of the rack L. A barcode including a rack ID is printed on the barcode label BL2.

Figure 3A:
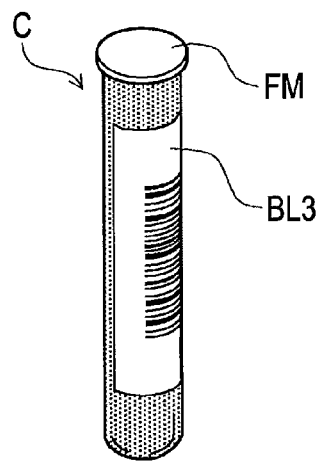
FIG. 3A is a view showing a washing fluid tube according to the embodiment.
Figure 3B:
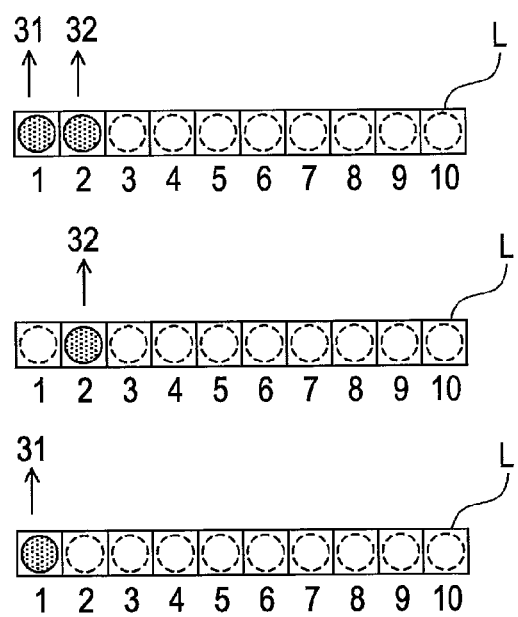
FIG. 3B is a view showing an arrangement rule of the washing fluid tube according to the embodiment.

FIG. 3A is a perspective view showing an external appearance of the washing fluid tube C, and FIG. 3B is a view showing an arrangement of the washing fluid tube C when the rack L is seen from the upper surface. In FIG. 3B, the upstream and downstream of the transporting direction and the numbers of the holding positions of the rack L shown in FIG. 2B are also shown.

With reference to FIG. 3A, the washing fluid tube C is a tube having a bottom and being made of colored glass or synthetic resin, and has an upper end opened. The color of the washing fluid tube C is different from the color of the sample tube T, so as to be easily distinguished visibly. The washing fluid contained inside the washing fluid tube C is chlorinated washing solution for washing the fluid circuit of the measurement units 31, 32. The opening at the upper end is sealed by a film FM to prevent lowering in chloride concentration of the washing fluid.

A barcode label BL3 is attached to the side surface of the washing fluid tube C. A barcode including a washing fluid ID is printed on the barcode label BL3. The washing fluid ID is identifiable from the sample ID. The washing fluid tube C has similar shape and size as the sample tube T, and may be held in a perpendicular state (upright state) in the rack L, similar to the sample tube T.

With reference to FIG. 3B, the washing fluid tube C is installed in the rack L according to a predetermined arrangement rule. The holding positions are installed with the washing fluid tube C in an order from the holding positions nearest to the downstream of the transporting direction so as to rapidly perform the washing operation. The holding position where the washing fluid tube C is installed defines one of the measurement units that uses the washing fluid tube C.

When washing is carried out on both the measurement unit 31 and the measurement unit 32, two washing fluid tubes C are installed at the holding position 1 and the holding position 2, as shown at the upper level of FIG. 3B. Normally, the other holding positions 3 to 10 are not installed with the sample tube T or the washing fluid tube C. In this case, the washing fluid tube C at the holding position 1 is allocated to the measurement unit 31, and the washing fluid tube C at the holding position 2 is allocated to the measurement unit 32.

The washing fluid tube C is installed only at the holding position 2, as shown in the middle level of FIG. 3B, when washing is carried out on the measurement unit 32 only. Similarly the washing fluid tube C is installed only at the holding position 1, as shown in the lower level of FIG. 3B, when washing is carried out on the measurement unit 31 only. In such cases, the washing fluid tube C is allocated to either one of the measurement units 31, 32.

Therefore, only the washing fluid tube C is normally installed in either one of or both of the holding position 1 and the holding position 2 of the rack L when washing the measurement units 31, 32.

Returning back to FIG. 1, the measurement unit 31 performs processing on the sample tube T on the rack transporting portion 23 on the front side of the relevant unit when measuring the sample. In other words, the measurement unit 31 picks up the sample tube T from the rack L with the hand portion 31a (see FIG. 4) and transports the sample tube T into the measurement unit 31 at the retrieving position P31a (see FIG. 4) of the rack transporting portion 23, so that the sample contained in the sample tube T is aspirated in the measurement unit 31. After aspiration is completed, the measurement unit 31 returns the sample tube T again to original position of the holding positions of the rack L. The measurement unit 32 also aspirates the sample in a manner similar to the measurement unit 31.

In case where a washing is carried out on the measurement unit, the measurement unit 31 performs processing on the washing fluid tube C on the rack transporting portion 23 on the front side of the unit. Similar to measuring the sample tube T, the measurement unit 31 picks up the washing fluid C from the rack L by the hand portion 31a (see FIG. 4) and transports the washing fluid tube C into the measurement unit 31 at the retrieving position P31a (see FIG. 4) of the rack transporting portion 23. The measurement unit 31 then aspirates the washing fluid contained in the washing fluid tube C and flows it to the flow path and the detector used in the measurement of the sample in the measurement unit 31. The washing fluid is also retained therein for a predetermined time to remove dirt.

Preferably the washing is carried out once a day. For the purpose, washing fluid is retained for a long time in the fluid path, the detector and the like. After aspiration of washing solution is completed, the measurement unit 31 returns the washing fluid tube C again to the original position of the rack L. The measurement unit 32 also performs washing in a manner similar to the measurement unit 31. The power of the washed measurement units 31, 32 is automatically shut down.

The information processing unit 4 includes an input section 41 and a display section 42. The information processing unit 4 is communicably connected to the transportation unit 2, the measurement units 31, 32, and a host computer 5 (see FIG. 8) through a communication network.

The information processing unit 4 controls the operations of the transportation unit 2 and the measurement units 31, 32. The information processing unit 4 makes an inquiry on the measurement order to the host computer 5 (see FIG. 8) when the sample ID is read by the barcode unit B2 (see FIG. 4). The information processing unit 4 performs analysis based on the measurement result performed by the measurement units 31, 32, and transmits the analysis result to the host computer 5 (see FIG. 8). The information processing unit 4 acquires a result of a determination by the host computer 5 (see FIG. 8) regarding whether a retest of the sample is necessary or not.

In the present embodiment, the retest is assumed to be carried out only once. Furthermore, retest in the present specification includes all measurements carried out by again aspirating the sample that is already aspirated and measured. Therefore, not only limited to again measuring the measurement item same as in the initial measurement, measuring a measurement item different from that in the initial measurement is also encompassed in the term "retest".

The information processing unit 4 can display information such as a warning message on the display section 42.

Figure 4:
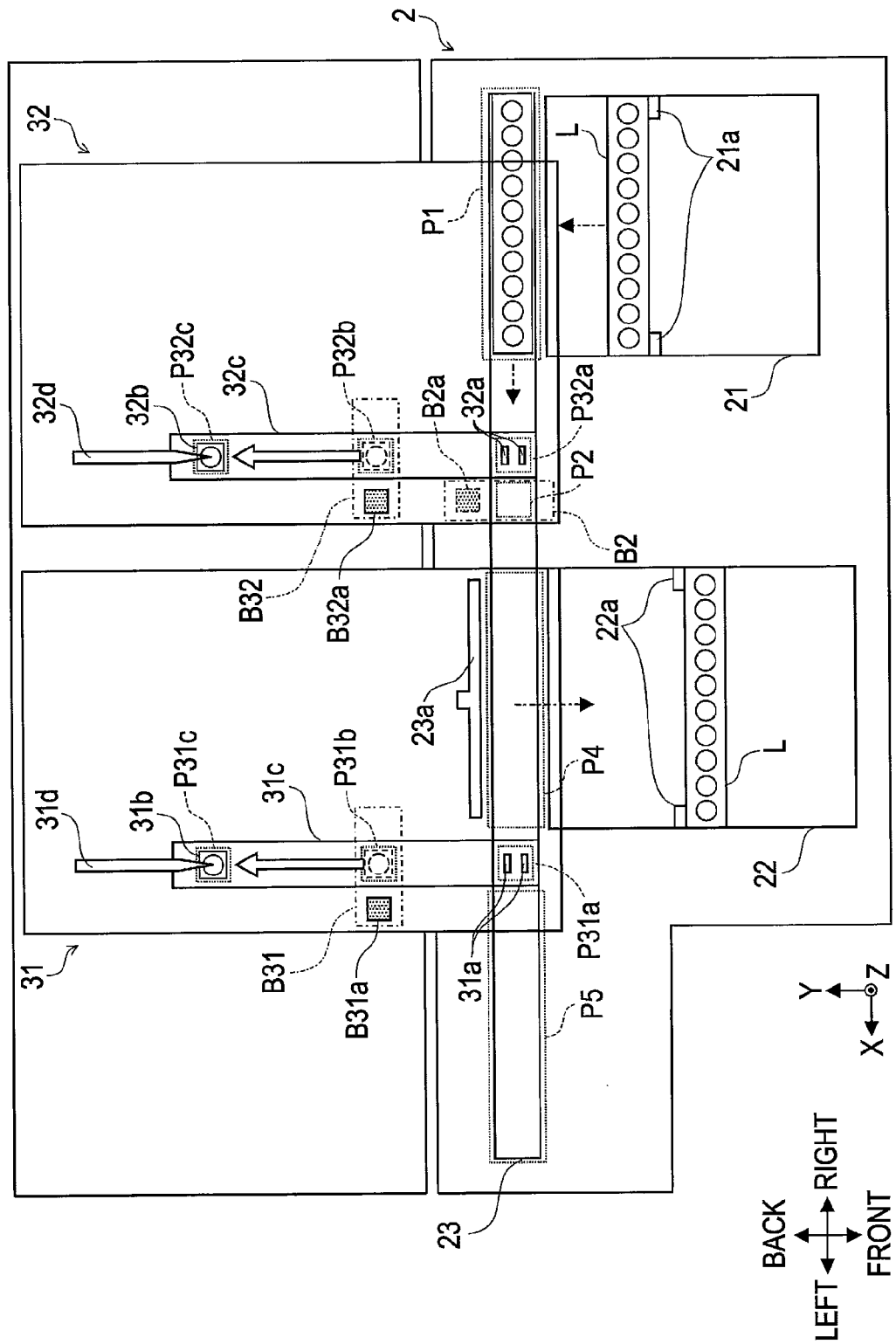
FIG. 4 is a plan view showing a configuration of a transportation unit and measurement units according to the embodiment viewed from an upper side.

FIG. 4 is a view schematically showing a configuration of the transportation unit 2 and the measurement units 31, 32 viewed from the upper side.

Hereafter, the reading operation of the barcode information will be described with reference to FIG. 4.

The rack L mounted on the right table 21 is transported to a feeding position P1 at the right end (most upstream position in the transporting direction) of the rack transporting portion 23 when the side surface on the front side is pushed by a rack feeding mechanism 21a. The rack L positioned at the feeding position P1 of the rack transporting portion 23 is transported towards the left direction by the belt (not shown) of the rack transporting portion 23. Two belts of the rack transporting portion 23 are arranged in parallel, where if two racks L are positioned in the rack transporting portion 23, each rack L is independently transported in the left and right direction by each belt.

The barcode unit B2 including the barcode reader B2a is provided near the middle of the rack transporting portion 23. When the holder of the rack L is positioned at the reading position P2 on the front side of the barcode reader B2a, whether or not a tube (sample tube T or washing fluid tube C) is held in the holder is determined by a holding determination mechanism (not shown) of the barcode unit B2. Such holding determination mechanism includes a mechanism capable of sandwiching the tube from two opposed sides. If the tube is sandwiched, determination is made that the tube is held in the holder positioned at the reading position P2.

If the sample tube T is held by the holder, the sample ID is read from the barcode label BL1 of the sample tube T by the barcode reader B2a while rotating the sample tube T, and if the washing fluid tube C is held by the holder, the washing fluid ID is read from the barcode label BL3 of the washing fluid tube C by the barcode reader B2a while rotating the washing fluid tube C. When the barcode label BL1 of the rack L is positioned in front of the barcode reader B2a, the rack ID is read from the barcode label BL2 of the rack L by the barcode reader B2a.

The barcode information of the rack L, and tube presence/absence information and the barcode information of all the holders at the holding positions 1 to 10 of the rack L are acquired in such manner.

The supply operation of the sample tube T and the washing fluid tube C of the rack L to the measurement units 31, 32 will now be described.

As described above, when the barcode information is read, the sample tubes T installed in the holder of the rack L are, in principle, supplied to in order of the measurement unit 31 and the measurement unit 32 in an order from the tube arranged at the holding position in the downstream (left direction) of the transporting direction. For instance, if the sample tubes T1, T2, and T3 are installed at the holding positions 1, 2, and 3 of the rack L, the sample tube T1 is positioned at the retrieving position P31a. At the retrieving position P31a, the hand portion 31a is provided movably in the up and down direction (Z axis direction). The sample tube T1 positioned at the retrieving position P31a is gripped by the hand portion 31a, picked up in the upward direction (positive direction in Z axis) from the rack L, and retrieved into the measurement unit 31.

After the sample tube T1 is picked up by the measurement unit 31, during the aspiration of the sample in the measurement unit 31, the sample tube T2 is positioned at a retrieving position P32a. The sample tube T2 positioned at the retrieving position P32a is gripped by the hand portion 32a, picked up in the upward direction (positive direction in Z axis) from the rack L, and retrieved into the measurement unit 32.

Thereafter, after the aspiration of the sample of the sample tube T1 is completed in the measurement unit 31, the holding position 1 of the rack L where the sample tube T1 has been arranged, is again positioned at the retrieving position P32a. The sample tube T1 gripped by the hand portion 31a of the measurement unit 31 is returned to the holding position 1 of the rack L from the upward direction (position direction in Z axis).

Subsequently the sample tube T3 is positioned at the retrieving position P31a and retrieved by the measurement unit 31.

Thus, the sample tubes T installed in the rack L are sequentially supplied to the measurement units 31, 32 in an alternate shift by positioning the odd-numbered holding position at the retrieving position P31a and positioning the even-numbered holding position at the retrieving position P32a by the rack transporting portion 23.

The retest of the sample becomes sometimes necessary after measurement and analysis. In such a case, the sample tube T that is already subjected to the initial measurement may be cut in an order of supplying tubes to the measurement units to be preferentially supplied to the measurement unit. In this case, the sample tube T containing the sample that needs a retest is supplied to either one of the measurement units in preference to the sample tube T that has not yet subjected to the initial measurement.

The supply of the washing fluid tube C to the measurement units 31, 32 is subjected to the arrangement rule shown in FIG. 3B. The washing fluid tube C at the holding position 1 is positioned at the retrieving position P31a and retrieved by the measurement unit 31. The washing fluid tube C at the holding position 2 is then positioned at the retrieving position P32a and retrieved by the measurement unit 32. If the washing fluid tube C is held only at the holding position 2, the washing fluid tube C is positioned at the retrieving position P32a and retrieved to the measurement unit 32 even if the tube is not supplied to the measurement unit 31.

Thus, the washing fluid tube C installed in the rack L is supplied to the measurement units 31 or 32 according to the arrangement rule shown in FIG. 3B by the rack transporting portion 23.

When the sample tube T is positioned at the retrieving position P31a or P32a, the sample tube T is automatically retrieved into the measurement unit 31 or 32, and the sample is aspirated. When the washing fluid tube C is positioned at the retrieving position P31a or P32a, the washing fluid tube C is automatically retrieved into the measurement unit 31 or 32, and the washing fluid tube is aspirated and washed is done. Such operation is carried out under the control of a CPU 401 (see FIG. 8) that will be described later.

FIG. 5A is a flowchart showing a retrieving operation of the sample tube T by the measurement unit 31 or 32.

With reference to FIG. 4 and FIG. 5A, when the sample tube T is positioned at the retrieving position P31a (P32a), the sample tube T is gripped by the hand portion 31a (32a), and picked up in the upward direction (positive direction in Z axis) (S31). The hand portion 31a (32a) then moves the sample tube T like a pendulum to stir the sample (S32). Then, the tube setting portion 31b (32b) is moved to the position above the retrieving position P31a (P32a) (S33). After finishing the stirring, the hand portion 31a (32a) is moved in the downward direction (negative direction in Z axis), and the sample tube T gripped by the hand portion 31a (32a) is set in the tube setting portion 31b (32b) (S34).

Thereafter, the tube setting portion 31b (32b) is transported to the barcode reading position P31b (P32b) (S35), and the sample tube T is checked by the barcode unit B31 (B32) including the barcode reader B31a (B32a) (S36).

The tube setting portion 31b (32b) is then positioned at the aspirating position P31c (P32c) at immediately below the piercing pipette 31d (32d) (S37). The piercing pipette 31d (32d) is then moved in the downward direction, and the sample is aspirated by the piercing pipette 31d (32d) from the sample tube T (S38).

After the aspiration of the sample by the piercing pipette 31d (32d) is finished, the tube setting portion 31b (32b) is moved to the front side and again positioned at the retrieving position P31a (P32a) (S39). At the retrieving position P31a (P32a), the sample tube T is retrieved in the upward direction by the hand portion 31a (32a) from the tube setting portion 31b (32b) (S40). The tube setting portion 31b (32b) is moved to the back side in this state. Thereafter, the hand portion 31a (32a) is moved in the downward direction (negative direction in Z axis), and the sample tube T is returned to the original holder of the rack L positioned in the rack transporting portion 23 (S41).

FIG. 5B is a flowchart showing a retrieving operation of the washing fluid tube C by the measurement unit 31 or 32.

In FIG. 5B, steps S51 and S52 to S60 are the same as S31 and S33 to S41 of FIG. 5A other than that a tube to be aspirated is the washing fluid tube C. Thus, the description of each step will be omitted herein. Emphasis should be made on the point that, in the retrieving operation of FIG. 5B, the step corresponding to S32 of FIG. 5A is skipped. This is because the washing fluid tube C does not need to be stirred.

In a case where the samples are measured, the sample tube T may possibly be supplied to the measurement unit 31 or 32 again for the retest of the sample even after the aspirations of all the samples are completed and all the sample tubes T are returned to the holders of the rack L. Normally, the time until the acquisition of the necessity of retest is acquired is longer than the time for the measurement of the sample in the measurement unit 31, 32 due to the communication of the measurement result to the information processing unit 4 and the host computer 5, the analyzing process of the measurement result, and the like (e.g., the measurement of the sample needs about 36 seconds, the time until acquisition of the necessity of retest is completed is about 75 seconds). Therefore, the rack L is waited on the rack transporting portion 23 until the acquisition of the necessity of retest of the sample of all the sample tubes T is completed.

A transportation space P5 longer than a length in the left and right direction of the rack L is provided in the left direction of the retrieving position P31a of the rack transporting portion 23. The rack L is positioned in the transportation space P5 until the acquisition of the necessity of retest for each of the samples of all the sample tubes T is completed. Thereby a space allowing to move the following rack on the rack transportation path is obtained.

After the process related to the retest is completed for all the sample tubes T, the rack L is positioned at the backward position of the left table 22, and transported to the front side of the left table 22 by a rack feeding mechanism 22a.

If the washing fluid tube C is held in the rack L, the washing liquid is aspirated for all the washing liquid tubes C, and thereafter, the rack L is positioned at the backward position of the left table 22, and transported to the front side of the left table 22 by the rack feeding mechanism 22a.

In such manner, the measuring process or the washing process is performed for all the racks L present at the right table 21.

FIG. 6 is a view showing an electrical connection relationship of the transportation unit 2 and the measurement unit 31, 32.

The transportation unit 2 includes a driving unit 201, a sensor unit 202, a barcode unit B2, and a communication unit 203.

The driving unit 201 includes a mechanism for transporting the rack L in the transportation unit 2, and the sensor unit 202 includes a sensor for detecting the rack L at a predetermined position on a transportation path of the transportation unit 2. The barcode unit B2 includes a holding determination mechanism (not shown), and a barcode reader B2a.

The communication unit 203 is communicably connected with the information processing unit 4. Each section of the transportation unit 2 is controlled by the information processing unit 4 through the communication unit 203. A signal output from each section of the transportation unit 2 is transmitted to the information processing unit 4 through the communication unit 203.

The measurement units 31, 32 respectively include an aspirating unit 311, 321, a specimen preparing unit 312, 322, a detection unit 313, 323, a driving unit 314, 324, a sensor unit 315, 325, a barcode unit B31, B32, and a communication unit 316, 326. The measurement units 31, 32 have exactly the same configuration, and thus only the measurement unit 31 will be described below.

Figure 7:
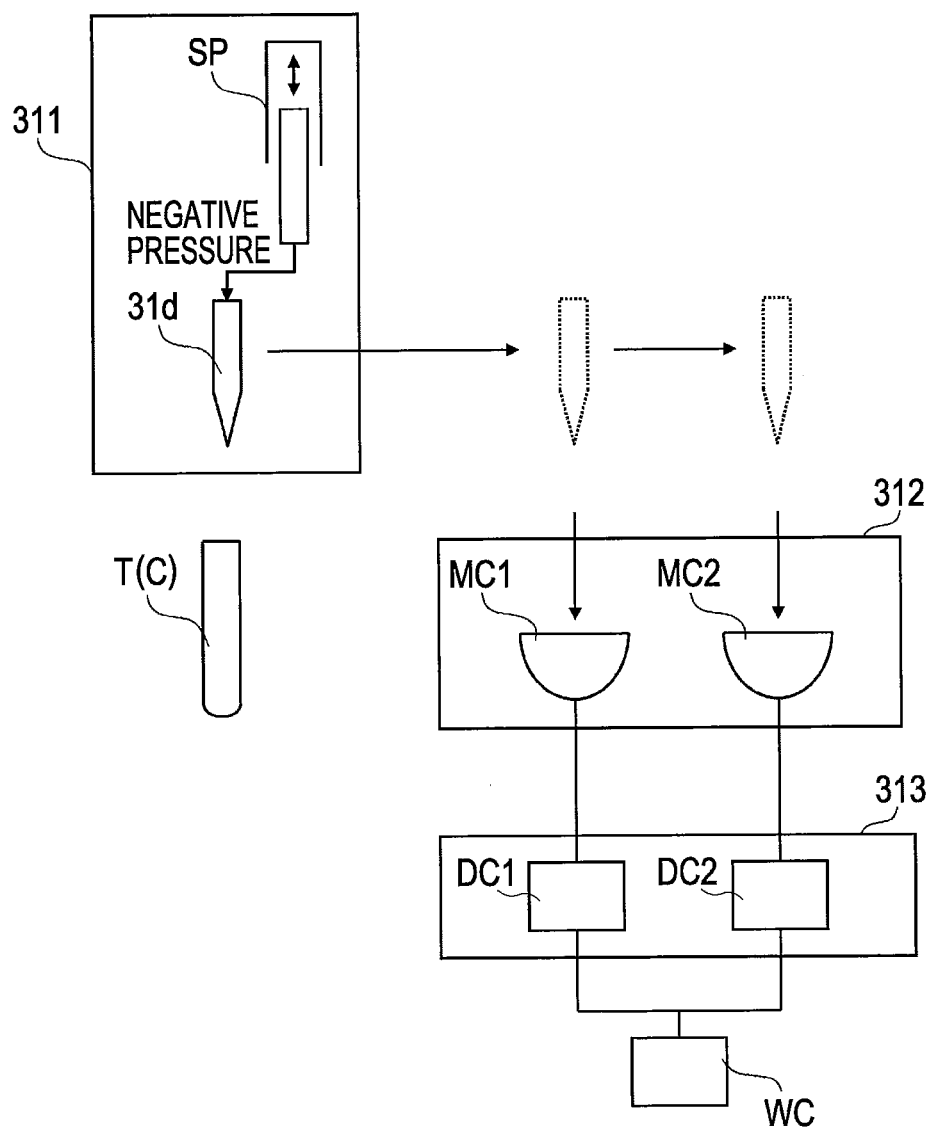
FIG. 7 is a view showing an outline of a fluid circuit of the measurement unit according to the embodiment.

FIG. 7 is a view showing an outline of a fluid circuit of the measurement unit 31. The measurement unit 31 is a blood cell counting apparatus configured to count blood cells contained in a whole blood sample.

The aspirating unit 311 includes a piercing pipette 31d for aspirating a sample contained in a sample tube T and a washing fluid contained in a washing fluid tube C taken into the measurement unit 31. Thereafter the piercing pipette is inserted to the tube, and a negative pressure generated by a syringe pump SP is applied to the piercing pipette 31d. The specimen preparing unit 312 includes a reaction chamber MC1 for preparing a specimen for measuring red blood cells and blood platelets, and a reaction chamber MC2 for preparing a specimen for measuring white blood cells. The detection unit 313 includes an electrical resistance detector DC1 for measuring red blood cells and blood platelets, and an optical detector DC2 for optically measuring white blood cells. The measurement unit 31 includes a waste fluid chamber WC for accommodating waste fluid.

When measuring the sample contained in the sample tube T, the aspirating unit 311 aspirates the sample through the piercing pipette 31d by applying negative pressure to the piercing pipette 31d with the syringe pump SP, and discharges the sample to each reaction chamber MC1, MC2. The specimen preparing unit 312 mixes sample and reagent in the reaction chamber MC1 to prepare a specimen for measuring red blood cells and blood platelets. The specimen preparing unit 312 mixes sample and reagent in the reaction chamber MC2 to prepare a specimen for measuring white blood cells. The specimen prepared in the reaction chamber MC1 is supplied to the electrical resistance detector DC1 through the flow path, and the specimen prepared in the reaction chamber MC2 is supplied to the optical detector DC2 through the flow path. The detection unit 313 detects optical signals (side fluorescent signal, forward scattered light signal, side scattered light signal, etc.) from white blood cells, nucleated red blood cells, and the like in the specimen as data of the sample with the optical detector DC2. The detection unit 313 also detects electrical signals from red blood cells and blood platelets in the specimen as data of the sample with the electrical resistance detector DC1. The specimen that passed the detection unit 313 is supplied to the waste fluid chamber WC through the flow path.

When performing washing using the washing fluid contained in the washing fluid tube C, the washing fluid is sent along the path similar to the sample. That is, washing fluid is aspirated from the washing fluid tube C by the aspirating unit 311 and discharged to each reaction chamber of the specimen preparing unit 312, so that the path from each reaction chamber to the waste fluid chamber WC is filled with washing fluid. It is left untouched in this state for a long time (about 30 minutes), and thereby residues of sample or reagent attached to the inner wall of the reaction chamber are removed.

Returning back to FIG. 6, the driving unit 314 includes a mechanism for transporting the sample tube T and the washing fluid tube C in the measurement unit 31. The sensor unit 315 includes a sensor for detecting a sample tube T or a washing fluid tube C at a predetermined position on the transportation path of the measurement unit 31. As described above, the barcode unit B31 includes a holding determination mechanism (not shown) and a barcode reader B31a.

The communication unit 316 is communicably connected with the information processing unit 4. Each section of the measurement unit 31 is controlled by the information processing unit 4 through the communication unit 316. A signal output from each section of the measurement unit 31 is transmitted to the information processing unit 4 through the communication unit 316.

Figure 8:
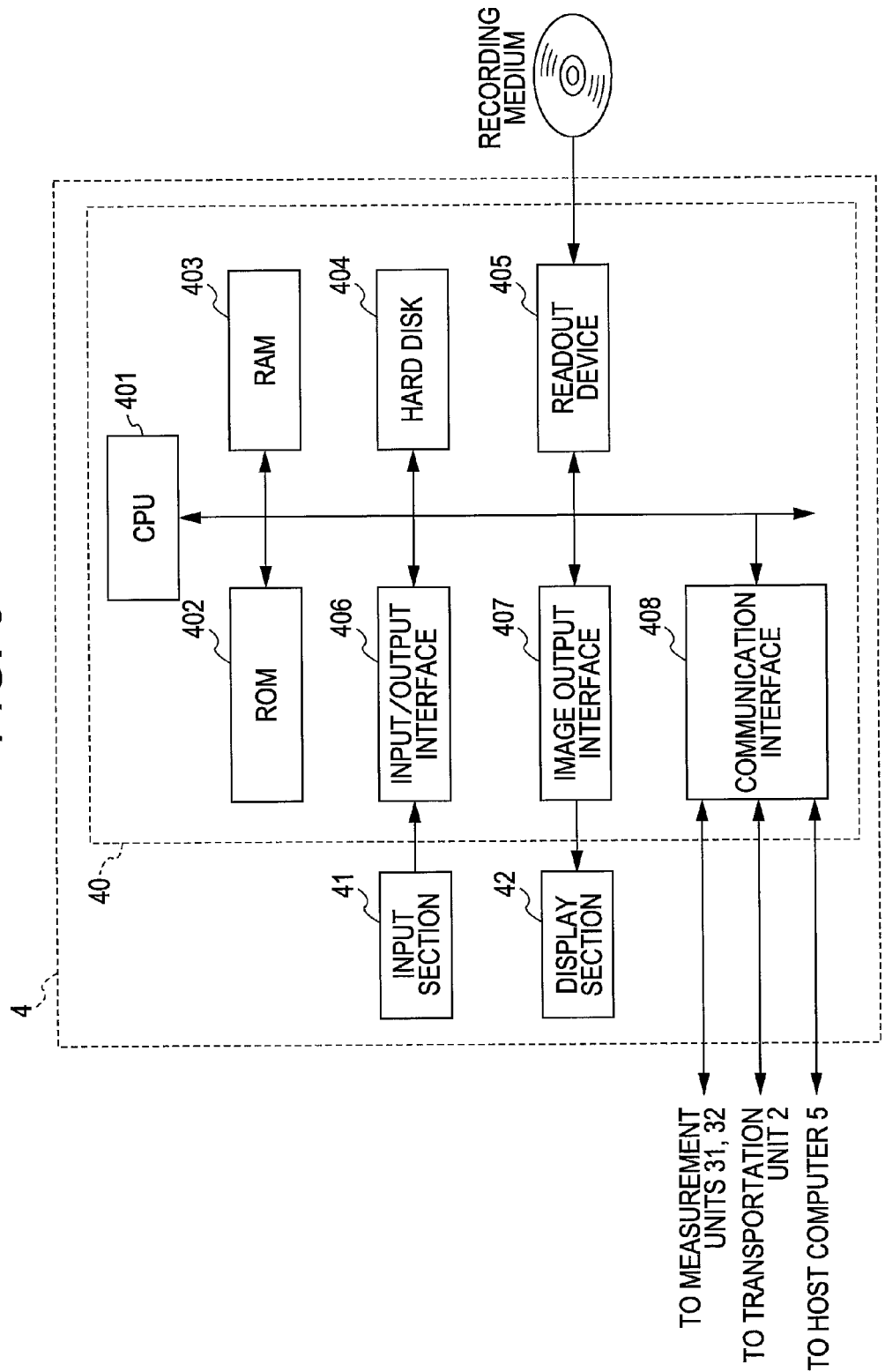
FIG. 8 is a view showing an outline of a configuration of an information processing unit according to the embodiment.

FIG. 8 is a view showing a configuration of the information processing unit 4.

The information processing unit 4 includes a personal computer and is configured by a main body 40, an input section 41, and a display section 42. The main body 40 includes a CPU 401, a ROM 402, a RAM 403, a hard disc 404, a readout device 405, an input/output interface 406, an image output interface 407, and a communication interface 408.

The CPU 401 can execute computer programs stored in the ROM 402 and the computer programs loaded in the RAM 403. The RAM 403 is used to read out the computer programs recorded on the ROM 402 and the hard disc 404. In executing the computer programs, the ROM 403 is used as a work area of the CPU 401.

The hard disc 404 is installed with various computer programs to be executed by the CPU 401 such as operating system and application programs, as well as data used in executing the computer program. In other words, the hard disc 404 is installed with a program for analyzing the data of the sample transmitted from the measurement units 31, 32 to generate measurement results of the number of red blood cells, the number of white blood cells, and the like, and making a display on the display section 42 based on the generated measurement results.

The readout device 405 includes a CD drive or DVD drive, and is capable of reading out a computer program or data recorded in a recording medium. The input section 41 including a mouse and a keyboard connected to the input/output interface 406, where the user uses the input section 41 to input instructions and data to the information processing unit 4. The display section 42 including a display connected to the image output interface 407, where a video signal corresponding to the image data is output to the display section 42.

The display section 42 displays the image based on the input video signal. Various types of program screens are displayed on the display section 42. The data is transmitted and received with respect to the transportation unit 2 and the measurement units 31, 32 by the communication interface 408.

Figure 9:
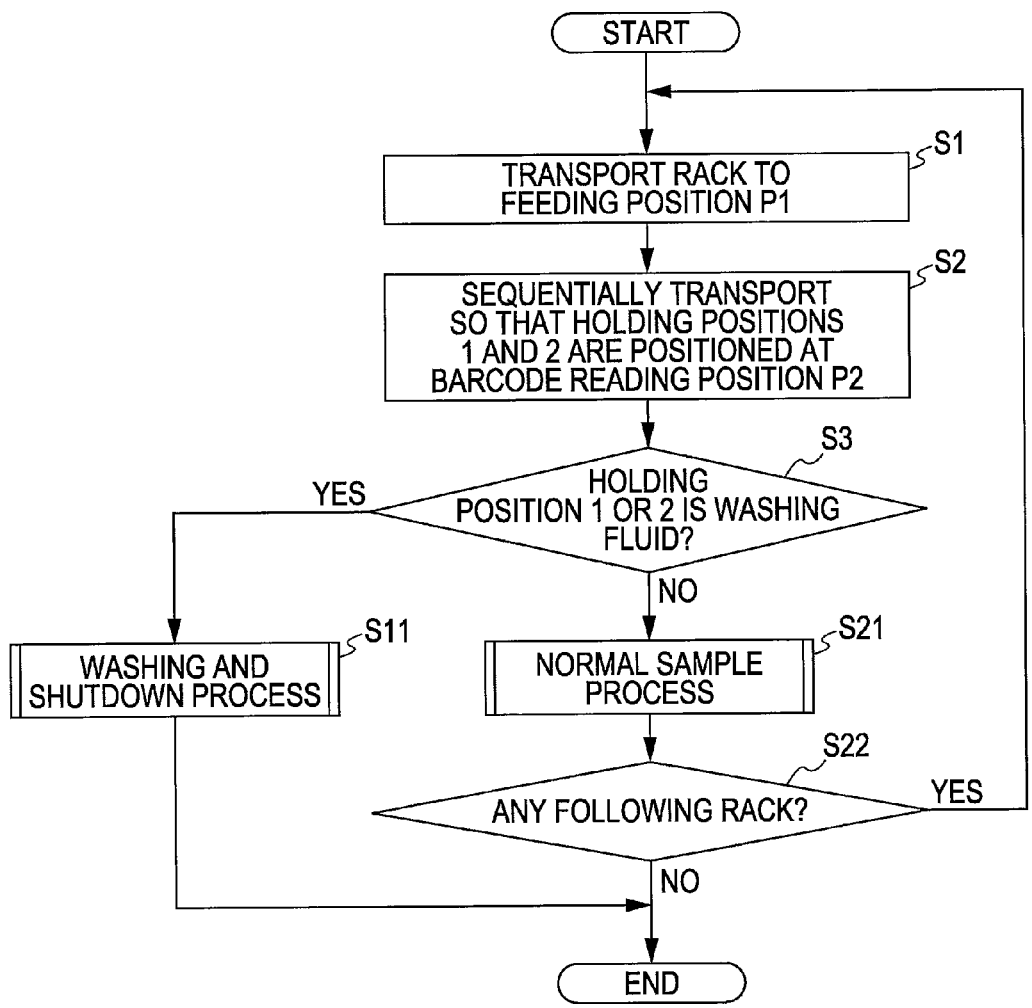
FIG. 9 is a view showing a flowchart of a transportation control of a rack according to the embodiment.

FIG. 9 is a flowchart of the control operation of the rack L by the CPU 401 of the information processing unit 4.

First, whether to perform a washing and a shutdown process or to perform a sample process is determined for the rack L according to the type of tube arranged in the holding positions 1 and 2 of the rack L.

Specifically, when the rack L is set in the right table 21, the CPU 401 operates the rack feeding mechanism 21a to transport the rack L to the feeding position P1 of the rack transporting portion 23 (S1). The CPU 401 operates the rack transporting portion 23 to transport the rack L so that the holding positions 1 and 2 of the rack L are positioned at the barcode reading position P2 (S2). For each of the holding positions 1 and 2, presence or absence of the tube is determined. If at least one of the holding positions 1 and 2 is installed with a tube, the barcode information of the detected tube is read by the barcode unit B2. The CPU 401 then determines whether a washing fluid tube C is installed with at least one of the holding position 1 or 2 (S3).

If the washing fluid tube C is at the holding position 1 or 2 (S3: YES), the CPU 401 executes the washing and shutdown process (S11). The details of the washing and shutdown process (S11) will be described later with reference to FIG. 10. The process on the rack L is then completed.

If the washing fluid tube C is not at either holding positions 1, 2 (S3: NO), the CPU 401 executes the normal sample process (S21). The details of the normal sample process (S21) will be described later with reference to FIG. 11.

When some steps in all steps of the normal sample process S21 is completed for the rack L, next rack L is allowed to be fed into the transportation path. The CPU 401 determines whether a rack L to be transported is present at the right table 21 (S22). Specifically, the timing the following rack L can be fed into the transportation path is the time when a necessity of retest is acquired for a predetermined number of sample tubes T of the rack L and it is determined that the preceding rack L does not need to be returned to the position of the feeding position P1 of the rack transporting portion 23. In the present embodiment, if it is determined that samples held at the holding positions 1 to 6 are not required to be retested, the preceding rack L may no longer be returned to the feeding position P1. Therefore, the following rack L can be positioned at the feeding position P1.

In such state, if a following rack L exists in the right table 21 (S22: YES), the process is returned to S1 so that the following rack L is transported to the feeding position P1, the processes described above will be repeated, and the sample process or the washing process will be performed.

If the following rack L does not exist in the right table (S22: NO), the process is completed for all the racks L.

Hereinafter, a processing flow will be described assuming a state where the preceding rack L1 is subjected to the normal sample process S21, and the following rack L2 following the preceding rack L1 is subjected to the washing and shutdown process S11.

Figure 10:
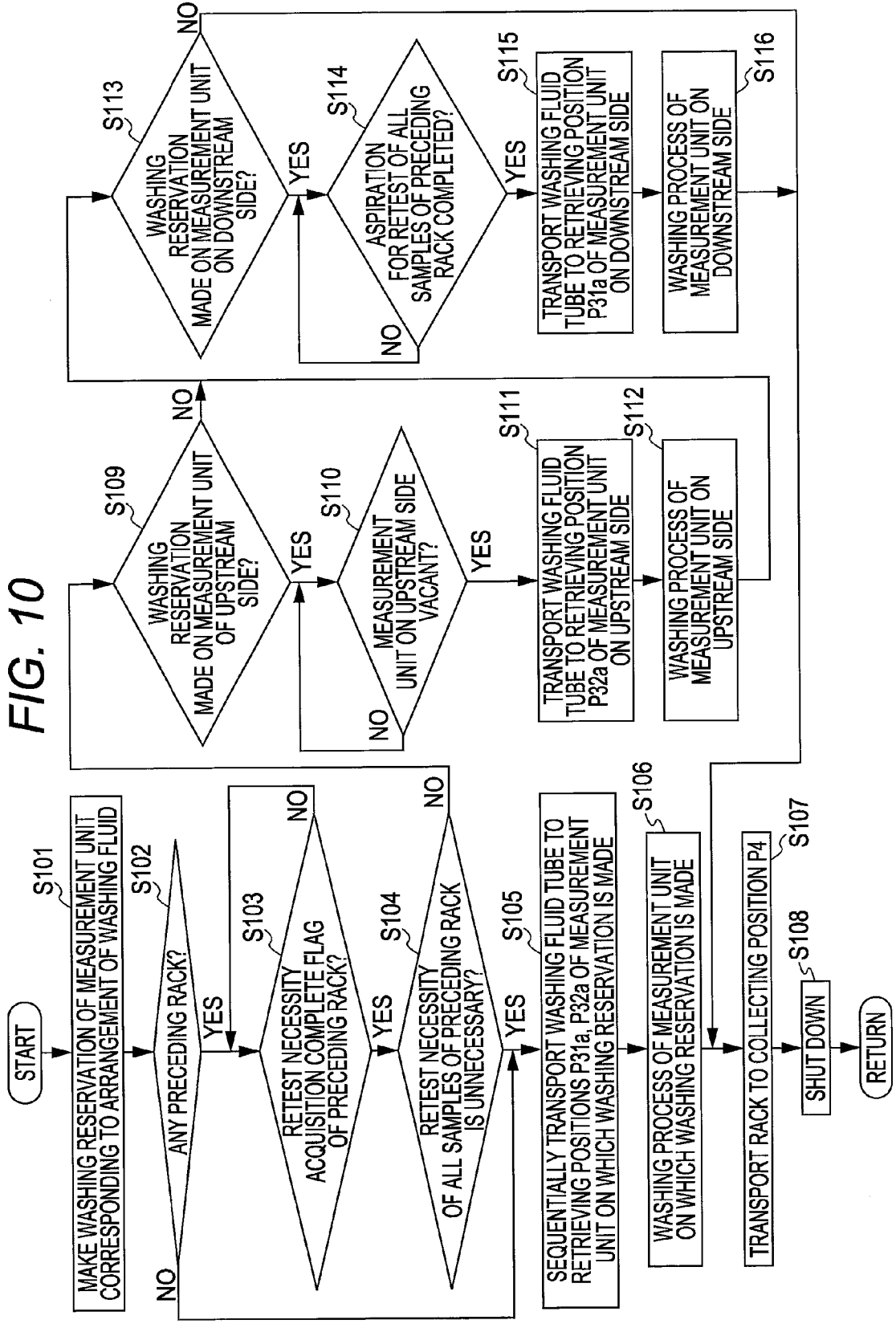
FIG. 10 is a view showing a flowchart of a transportation control of a rack at time of washing and shutdown according to the embodiment.

FIG. 10 is a flowchart of control operation of the following rack L2 by the CPU 401 in the washing and shutdown process of S11 of FIG. 9.

If a washing fluid tube C is arranged at the holding position 1 or the holding position 2 of the following rack L2 by the process shown in FIG. 9, the CPU 401 makes a washing reservation of the measurement unit corresponding to the arrangement of the washing fluid tube C (S101). For instance, if the washing fluid tube C is set in both the holding position 1 and the holding position 2, the reservation for washing is made on both of the measurement units 31 and the measurement unit 32. If the washing fluid tube C is set only in the holding position 1, the reservation for washing is made only on the measurement unit 31.

The CPU 401 then determines whether or not the preceding rack L1 preceding the following rack L2 exists on the rack transporting portion 23 (S102). If the preceding rack L1 does not exist on the rack transporting portion 23 (S102: NO), the CPU 401 proceeds the process to S105, whereas if the preceding rack L1 exists on the rack transporting portion 23 (S102: YES), the CPU 401 determines whether or not a retest necessity acquisition complete flag of the preceding rack L1, to be described later, is set (S103). If the acquisition of retest necessity is completed from the host computer 5 for all the samples of the preceding rack L1, the retest necessity acquisition complete flag is set, and if the retest necessity acquisition is not completed, the retest necessity acquisition complete flag is not set.

If the retest necessity acquisition complete flag of the preceding rack L1 is not set (S103: NO), the CPU 401 waits for the subsequent processes until the retest necessity acquisition complete flag of the preceding rack L1 is set. If the retest necessity acquisition complete flag of the preceding rack L1 is set (S103: YES), the CPU 401 further determines whether retest is unnecessary for any of the samples of the preceding rack L1 (S104).

If retest is unnecessary for any of the samples of the preceding rack L1 (S104: YES), the CPU 401 operates the transporting portion 23 to transport the washing fluid tube C to the retrieving positions P31a or P32a corresponding to the measurement units 31 or 32 on which washing reservation has been made (S105). In the measurement units 31 or 32 on which the washing reservation is made, the washing process using the transported washing fluid tube C is carried out (S106). The washing includes the task of retaining the washing fluid in the fluid circuit of the measurement unit over a long time (about 30 minutes). As will be described later, the time from when the sample is aspirated until the measurement and the determination on the necessity of retest are completed takes 75 seconds, and hence the time required for washing is longer than the time required from aspiration to the determination on the necessity of retest.

If the retest is not unnecessary (S104: NO) for all the samples of the previous rack L1, in other words, when one or more of samples of the previous rack L1 need to be subjected to the retest, the CPU 401 determines whether or not the washing reservation is made on the measurement unit 32 which is provided on the upstream side in the transporting direction (S109). If the washing reservation is not made on the measurement unit 32 (S109: NO), the CPU 401 proceeds the process to S113, and if the washing reservation is made on the measurement unit 32 (S109: YES), the CPU 401 determines whether the measurement unit 32 on the upstream side is vacant (S110). The "vacant" means a state where any sample is not processing by the measurement unit 32. If the measurement unit 32 is performing the retest and is not vacant (S110: NO), the CPU 401 waits for the following process until the measurement unit 32 becomes a vacant state. If the measurement unit 32 is vacant (S110: YES), the CPU 401 operates the rack transporting portion 23 to transport the washing fluid tube C to the retrieving position P32a corresponding to the measurement unit 32 (S111). In the measurement unit 32, the washing process using the washing fluid tube C is carried out (S112). In this case, the retest of the sample is carried out in the measurement unit 31 on the downstream side for the sample in which the retest has not started yet.

The CPU 401 determines whether or not the washing reservation has been made on the measurement unit 31 on the downstream side in the transporting direction (S113). If the washing reservation has not been made on the measurement unit 31 (S113: NO), the CPU 401 proceeds the process to S107, and if the washing reservation has been made on the measurement unit 31 (S113: YES), the CPU 401 determines whether an aspiration for the retest is completed for all the samples of the preceding rack L1 (S114).

If an aspiration for the retest is not completed (S114: NO) for all the samples of the preceding rack L1, the CPU 401 waits for the following process until the aspiration for the retest is completed for all the samples of the preceding rack L1. If the aspiration is completed (S114: YES), the sample of the preceding rack L1 will not be supplied to the measurement unit 31, and hence the CPU 401 operates the rack transporting portion 23 to transport the washing fluid tube C to the retrieving position P31a corresponding to the measurement unit 31 (S115). In the measurement unit 31, the washing process using the washing fluid tube C is carried out (S116).

After the washing processes of the measurement units 31 and 32 are completed, the CPU 401 operates the rack transporting portion 23 to transport the following rack L2 to the collecting position P4 (S107). The following rack L2 transported to the collecting position P4 is discharged to the left table 22 by a rack pushing mechanism 23a. Thereafter, when washing for both measurement units 31, 32 is completed, the CPU 401 shuts down the measurement units 31, 32 and the information processing unit 4 (S108). If washing is completed for only one of the measurement units 31 or 32, the shutdown process of the measurement units 31 and 32 and the information processing unit 4 is not executed, and the shutdown is executed only after washing of both measurement units 31 and 32 is completed.

Thus, if there is a sample in which the retest is not completed at the stage where the acquisition of the retest necessity is completed for all the samples of the preceding rack L1, the CPU 401 performs the washing process on one of the measurement units 31 and 32 while leaving the remaining one of the measurement unit 31 and 32. The remaining measurement unit will be washed after aspiration for the retest is completed for all the samples of the preceding rack L1. The CPU 401 thereby completes the process on the following rack L2.

Figure 11A:
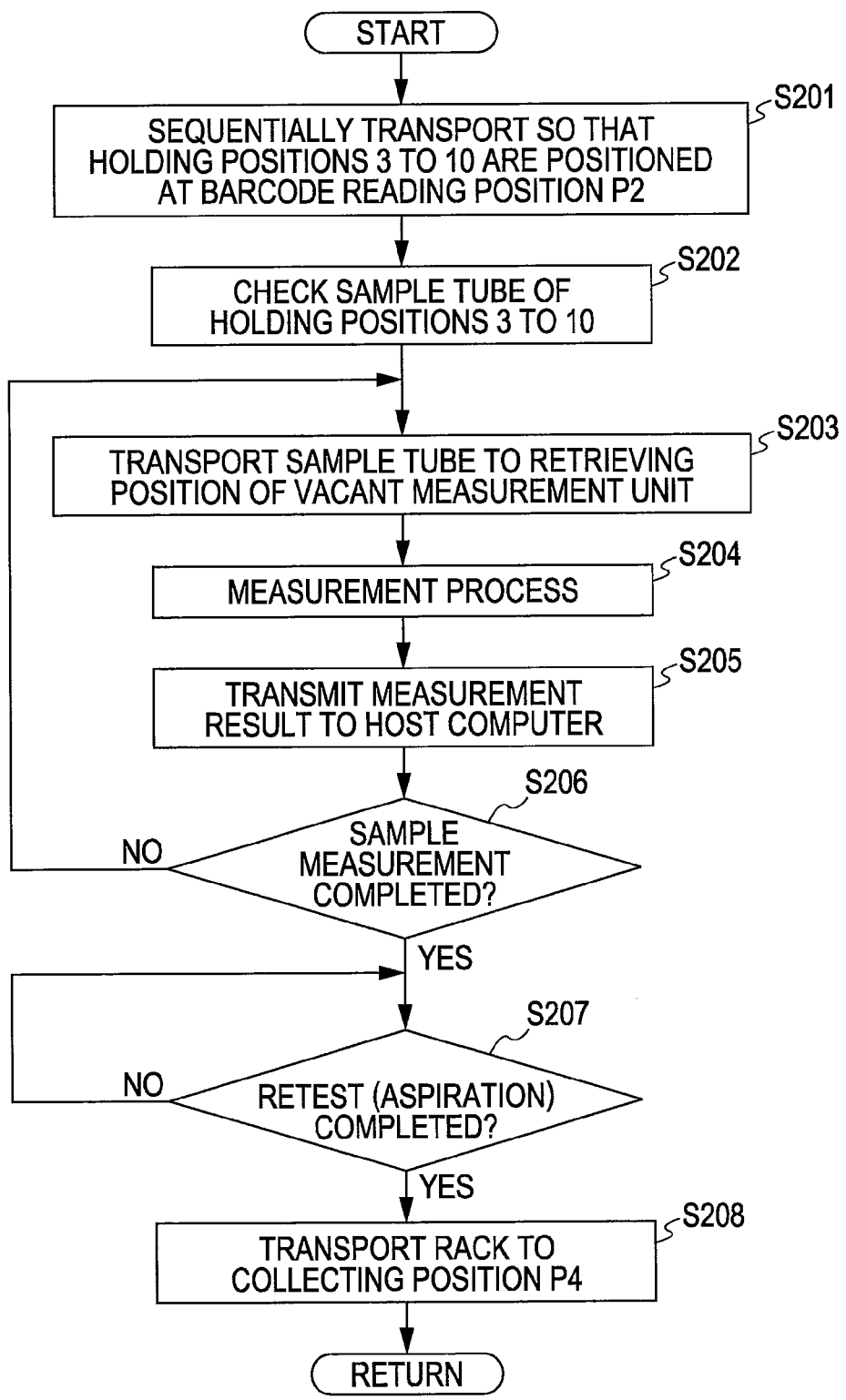
FIG. 11A is a view showing a flowchart of transportation control process for normal sample according to the embodiment.

FIG. 11A is a flowchart showing an operation of the preceding rack L1 by the CPU 401 at the time of the normal sample process of S21 of FIG. 9.

If the washing fluid tube C is not contained in either the holding position 1 nor the holding position 2 of the preceding rack L1 by the process shown in FIG. 9, the CPU 401 operates the rack transporting portion 23 to transport the preceding rack L1 so that the following holding positions 3 to 10 are sequentially positioned at the barcode reading position P2 (S201). In this case, the presence or absence of the tube at each holding position is determined by the barcode unit B2, and the barcode information of the tube installed at each holding position is read (S202).

The CPU 401 then operates the rack transporting portion 23 to transport the sample tubes T to the retrieving position P31a or the retrieving position P32a (S203). As described above, the sample tubes T are distributed to the measurement units 31, 32 in an order from the downstream in the transporting direction. If both measurement units 31 and 32 are in measurement, the CPU 401 waits until the measurement in either one of the measurement units is completed. If a holder is not installed with a sample tube or the holder is installed with a washing fluid tube C, the holder will be skipped. The CPU 401 then operates the measurement units 31, 32 to aspirate a sample in the transported sample tube T, to perform a measurement, and to generate a measurement result (S204). The measurement result is transmitted via the information processing unit 4 to the host computer 5 (S205).

The host computer 5 determines the necessity of retest based on the received measurement result, and transmits the determination result on the necessity of retest to the information processing unit 4. The necessity of retest is determined by whether or not the received measurement result is within a numerical value range indicating a normal measurement result. More specifically, if the measurement result of a certain sample is within the numerical value range, the host computer 5 assumes that such sample is normal, determines that retest for such sample is unnecessary, and transmits the determination result that the retest is unnecessary. If the measurement result of a certain sample is not within the numerical value range, the host computer 5 assumes that the sample is abnormal or the measurement operation is abnormal, and thus determines that retest is necessary for such sample. If determined that the retest is necessary, the host computer 5 further automatically generates the measurement order including the measurement item to be measured in the retest, and transmits the measurement order with the determination result indicating that the retest is necessary.

Figure 11B:
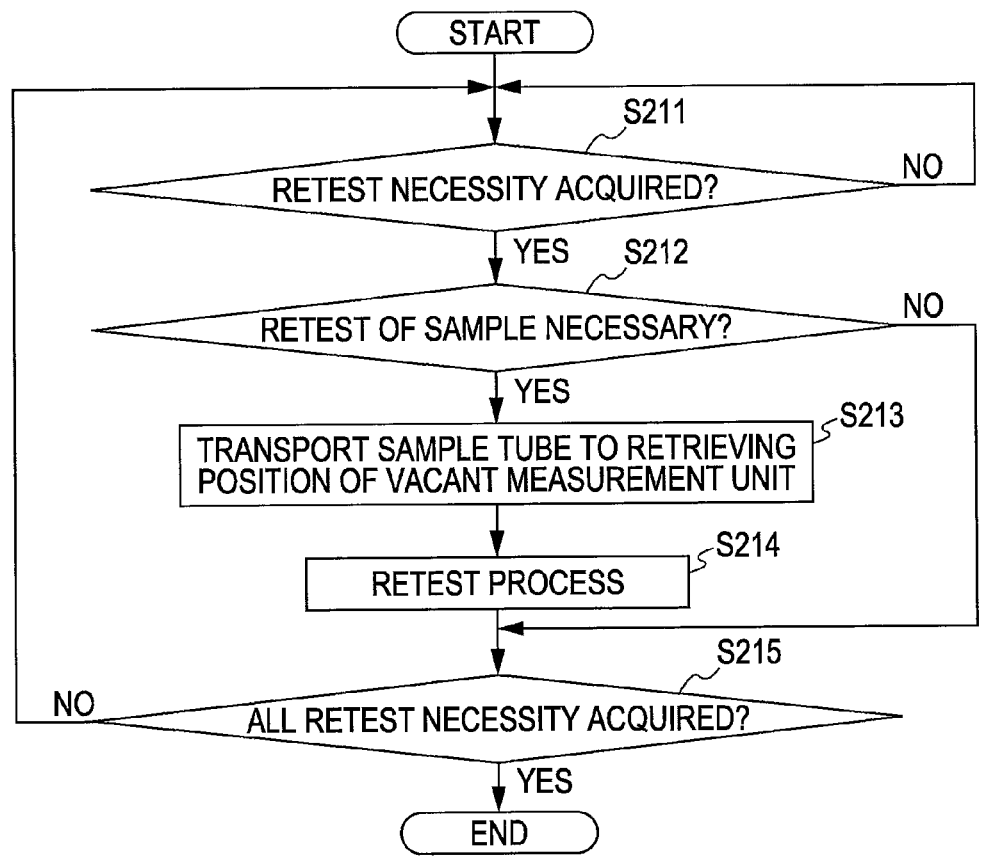
FIG. 11B is a view showing a flowchart of retest process for normal sample according to the embodiment.

FIG. 11B is a flowchart showing a flow of operation of the retest process at the time of the normal sample process. The relevant process is started when the normal sample process is started.

With reference to FIG. 11B, the CPU 401 first determines whether the determination result of the retest necessity is acquired from the host computer 5 for a sample (S211). If the determination result of the retest necessity is not acquired (S211: NO), the CPU 401 waits for the following process until the determination result is acquired. If the determination result of the retest necessity is acquired (S211: YES), the CPU 401 determines whether or not the retest is necessary for the sample based on the acquired determination result (S212).

The CPU 401 proceeds the process to S215 if the retest of the sample is not necessary (S212: NO), and if the retest of the sample is necessary (S212: YES), the CPU 401 operates the rack transporting portion 23 to transport the sample tube T that accommodates the sample to be retested to the retrieving position 31a or the retrieving position 32a (S213). And the CPU 401 operates the measurement unit to perform the retest process on the sample according to the measurement order received with the determination result (S214), similar to the measurement process. The retest process cuts into the normal sample process, and is carried out prior to the normal sample process.

The CPU 401 then determines whether or not the determination result of the retest necessity is acquired for all the samples of the preceding rack L1 (S215). If the determination result of the retest necessity is not acquired for all the samples of the preceding rack L1 (S215: NO), the CPU 401 repeats the steps S211 to S215 until the determination results of all the samples are acquired. When the determination result of the retest necessity is acquired for all the samples of the preceding rack L1 (S215: YES), the CPU 401 completes the retest process on the preceding rack L1.

Returning back to FIG. 11A, after transmitting the measurement result to the host computer 5, the CPU 401 determines whether or not measurements for all the samples of the preceding rack L1 are completed (S206). If measurements for all the samples of the preceding rack L1 are not completed (S206: NO), the CPU 401 repeats the processes S203 to S206. As described above, if a necessity of retest occurs during the sequential measurements of the samples, the retest process is preferentially carried out.

After measurements of all the samples of the preceding rack L1 are completed (S206: YES), the CPU 401 waits until the aspiration for the retest is completed for all the samples of the preceding rack L1. When the aspiration for the retest is completed (S207: YES) for all the samples of the preceding rack L1, the CPU 401 operates the rack transporting portion 23 to transport the preceding rack L1 to the collecting position P4 (S208). The preceding rack L1 transported to the collecting position P4 is discharged to the left table 22 by the rack pushing mechanism 23a. The washing fluid tube C of the following rack L2 is thereby supplied to the measurement unit 31 on the downstream side. The CPU 401 therefore completes the normal sample process on the preceding rack L1.

Figure 11C:
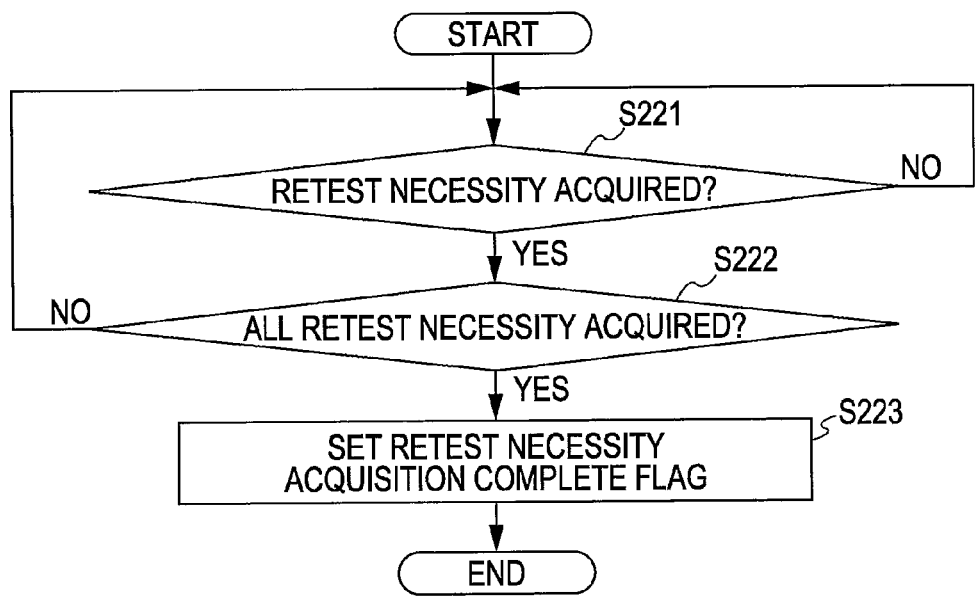
FIG. 11C is a view showing a flowchart of flag setting process for normal sample according to the embodiment.

FIG. 11C is a flowchart showing a flow of the setting process of the retest necessity acquisition complete flag. This flow is started when the normal sample process is started.

With reference to FIG. 11C, the CPU 401 first waits for the determination result about the necessity of retest sent from the host computer 5 (S221). When the determination result is acquired (S221: YES), the CPU 401 determines whether or not the determination result is acquired for all the samples of the preceding rack L1 (S222). When the determination result is acquired for all the samples of the preceding rack L1 (S222: YES), the CPU 401 sets the retest necessity acquisition complete flag (S223). The setting process of the retest necessity acquisition complete flag is thereby completed. When the retest necessity acquisition complete flag is set, the determination of S103 of FIG. 10 becomes YES and the processes after S104 are proceeded.

FIG. 12 is a view showing an operation state of the rack transporting portion 23 of the preceding rack L1 and the following rack L2 when the determination of the retest necessity from the host computer 5 is "unnecessary" for all the samples of the preceding rack L1. The sample tubes T are held in the holding positions 1 to 10 in the preceding rack L1, and only the washing fluid tube C is held in the holding positions 1 and 2 in the following rack L2.

FIG. 12A is a view showing a state of when the following rack L2 is positioned at the feeding position P1. Such state corresponds to a state in which the CPU 401 is processing the measurement process of S203 to S206 of FIG. 11A, the retest process of FIG. 11B, and the flag setting process of FIG. 11C in parallel for the preceding rack L1 and processing S1 of FIG. 9 for the following rack L2.

With respect to the sample tubes T installed in the holding positions 1 to 6 of the preceding rack L1, the retest necessity is already acquired, and determination is made that retest is unnecessary. The sample tubes T installed at the holding positions 7, 8 of the preceding rack L1 are supplied to the measurement units 31, 32. In this case, the sample tubes T installed at the holding positions 1 to 6 of the preceding rack L1 are not supplied to the measurement units 31, 32, and the preceding rack L1 will not be returned to the feeding position P1. The following rack L2 is thereby positioned at the feeding position P1.

FIG. 12B is a view showing a state of when the tube type of the holding positions 1, 2 of the following rack L2 is identified. Such state corresponds to a state in which the CPU 401 processes the measurement process of S203 to S206 of FIG. 11A, the retest process of FIG. 11B, and the flag setting process of FIG. 11C in parallel for the preceding rack L1, and processes S3 of FIG. 9 for the following rack L2.

With respect to the sample tubes T installed in the holding positions 1 to 7 of the preceding rack L1, the retest necessity is already acquired, and determination is made that retest is unnecessary. The sample tubes T installed at the holding positions 9, 10 of the preceding rack L1 are supplied to the measurement units 31, 32. The following rack L2 has the holding positions 1, 2 positioned at the barcode reading position P2, and the tubes installed in the holding positions 1, 2 are identified as the washing fluid tubes C.

FIG. 12C is a view showing a state when the measurement process of the sample tube T of all the holders of the preceding rack L1 is completed. Such state corresponds to a state in which the CPU 401 is processing the completion waiting process of the aspiration for the retest of S207 of FIG. 11A, the retest process of FIG. 11B, and the flag setting process of FIG. 11C in parallel for the preceding rack L1 and processing the retest necessity acquisition complete waiting of S103 of FIG. 10 for the following rack L2.

In the preceding rack L1, when the measurement of the sample tube T of the holding position 10 is completed, the sample tube T is returned from the measurement unit 32 to the preceding rack L1. In this case, the preceding rack L1 is determined that the retest necessity is already acquired and the retest is unnecessary for the sample tubes T at the holding positions 1 to 8. The following rack L2 is evacuated to the feeding position P1 to wait thereat since the tubes installed at the holding positions 1, 2 are identified as the washing fluid tubes C but the acquisition of retest necessity of all the samples of the preceding rack L1 is not completed.

FIG. 12D is a view showing a state of when the measurement process of the sample tube T of all the holders of the preceding rack L1 is completed, the state being before the retest necessity is acquired. Such state corresponds to a state in which the CPU 401 is processing the completion waiting process of the aspiration for the retest of S207 of FIG. 11A, the retest process of FIG. 11B, and the flag setting process of FIG. 11C in parallel for the preceding rack L1 and processing the retest necessity acquisition complete waiting of S103 of FIG. 10 for the following rack L2.

The preceding rack L1 waits in the transportation space P5 of the rack transporting portion 23 so that the preceding rack L1 does not interfere the processing of the following rack L2 after the measurement process of the sample tube T of all the holders at the holding positions 1 to 10 is completed. In this case, samples in the sample tubes T at the holding positions 1 to 9 other than the holding position 10 are determined that the retest for each of them is unnecessary. In this case, the measurement units 31, 32 are vacant, but the following rack L2 waits at the feeding position P1 since the retest necessity acquisition of all the samples of the preceding rack L1 is not completed.

FIG. 12E is a view showing a state of when the retest necessity is acquired for the sample tubes T of all the holders of the preceding rack L1. Such state corresponds to a state in which the retest process of FIG. 11B and the flag setting process of FIG. 11C are completed, and the CPU 401 is processing S208 of FIG. 11A for the preceding rack L1 and starting the washing processes of S105 and S106 of FIG. 10 for the following rack L2.

For each of the samples in the sample tubes T of all the holders at the holding positions 1 to 10 of the preceding rack L1, it has been determined that the retest is unnecessary. The preceding rack L1 is then positioned at the collecting position P4, and pushed away to the left table 22. The following rack L2 supplies the washing fluid tube C to the measurement units 31, 32.

FIG. 13 is a view showing an example of an operation state of the rack transporting portion 23 of the preceding rack L1 and the following rack L2 when the determination of the retest necessity from the host computer 5 indicates "necessary" for the samples installed at the holding positions 9, 10 of the preceding rack L1.

FIGS. 13A and 13B are views showing a state of when the measurement process of the sample tube T of all the holders of the preceding rack L1 is completed, the state being before the retest necessity is acquired. Such state corresponds to a state in which the CPU 401 is processing the completion waiting process of the aspiration for the retest of S207 of FIG. 11A, the retest process of FIG. 11B, and the flag setting process of FIG. 11C in parallel for the preceding rack L1 and processing the retest necessity acquisition complete waiting of S103 of FIG. 10 for the following rack L2.

With reference to FIG. 13A, the preceding rack L1 waits in the transportation space P5 of the rack transporting portion 23 so that the preceding rack L1 does not interfere the processing of the following rack L2. In this case, for the samples in the samples tubes T at the holding positions 1 to 9, the retest necessity is already acquired. Further, it is determined that the retest is unnecessary for the sample tubes T at the holding positions 1 to 8, and the retest is necessary for the sample tube T at the holding position 9. The following rack L2 is evacuated to the feeding position P1 to wait thereat since the tubes installed at the holding positions 1, 2 are identified as the washing fluid tubes C but the acquisition of retest necessity of all the samples of the preceding rack L1 is not completed.

When it is determined that the retest is necessary for the sample tube T at the holding position 9 of the preceding rack L1, the sample tube T at the holding position 9 of the preceding rack L1 is supplied to the measurement unit 31 on the downstream side, as shown in FIG. 13B. In this case, the measurement unit 32 is vacant, so it is possible to initiate a washing for the measurement unit 32. But, the following rack L2 does not supply the washing fluid tube C to the measurement unit 32 and waits at the feeding position P1, since the retest necessity acquisition of all the samples of the preceding rack L1 is not completed.

FIG. 13C is a view showing a state when the acquisition of the retest necessity of the sample tube T of all the holders of the preceding rack L1 is completed and some of the samples in the sample tubes T are determined to be necessary to be retested. Such state corresponds to a state in which the CPU 401 is processing the completion waiting process of the aspiration for the retest of S207 of FIG. 11A, the retest process of FIG. 11B, and the flag setting process of FIG. 11C in parallel for the preceding rack L1 and processing the washing of the measurement unit 32 on the upstream side of S109 to S112 of FIG. 10 for the following rack L2.

With reference to FIG. 13C, the retest necessity is acquired for each of the samples in the sample tubes T held by the preceding rack L1, and the aspiration for the retesting the sample in the sample tube T at the holding position 9 is completed. The sample tube T at the holding position 10 is determined that the retest is necessary and is supplied to the measurement unit 31. The following rack L2 supplies the washing fluid tube C at the holding position 2 only to the measurement unit 32 since the retest necessity acquisition of all the samples of the preceding rack L1 has been completed, but the retest is necessary for the sample of the preceding rack L1.

FIG. 13D is a view showing a state when the aspiration for the retest is completed for the sample tubes T of all the holders of the preceding rack L1. Such state corresponds to a state in which the CPU 401 is processing the process of S208 of FIG. 11A for the preceding rack L1, and starting the washing process of the measurement unit 31 on the downstream side of S115, S116 of FIG. 10 for the following rack L2.

In the preceding rack L1, the aspirations for the retests of the samples held by the holding positions 9 and 10 are completed, and therefore none of samples in the preceding rack L1 needs to be aspirated for a retest once more. The preceding rack L1 is then positioned at the collecting position P4, and pushed away to the left table 22. In the following rack L2, the washing fluid tube C is supplied to the measurement unit 31 on the downstream side.

As described above, when it is identified that the holder of the following rack L2 includes one or more washing fluid tubes C and there is the preceding rack L1, the supply of the washing fluid tube C of the following rack L2 to the measurement units 31, 32 is suspended until the retest necessity acquisition of all the samples of the preceding rack L1 is completed.

Furthermore, if one or more samples in the preceding rack L1 is determined as necessary to be retested, the supply of the washing fluid tube C of the following rack L2 is suspended for at least one measurement unit until the aspiration for all the retests of the preceding rack L1 is completed.

If the determination result of the retest necessity is unnecessary for all the samples of the preceding rack L1, the washing fluid tube C of the following rack L2 is supplied to the measurement units 31, 32.

If the determination result of the retest necessity is necessary for a sample of the preceding rack L1, the retest of the sample is carried out. After the aspiration for the retest of the sample is completed and the aspiration for the retest is completed for all the samples of the preceding rack L1, the washing fluid tube C of the following rack L2 is supplied to the measurement units 31, 32.

Furthermore, the following rack L2 is waited at the feeding position P1 and the preceding rack L1 is waited in the transportation space P5 until the acquisition of the retest necessity of the sample tube T of the preceding rack L1 is completed.

According to the present embodiment, if the following rack L2 installed with the washing fluid tube C follows the preceding rack L1 installed with the sample tube T, the washing by the following rack L2 is suspended until the determination result of the retest necessity is acquired for all the samples of the preceding rack L1. Thus, a washing of a measurement unit is prevented to be initiated until all samples are determined as unnecessary to be retested. Therefore, any retest may not be interfered by a washing that has been already initiated, so the retest can be smoothly carried out.

According to the present embodiment, the following rack L2 is waited at the feeding position P1 until the acquisition of the retest necessity of the preceding rack L1 is completed, and thus the retest of the preceding rack L1 can be smoothly carried out without inhibiting the transportation control of the preceding rack L1.

According to the present embodiment, if the acquisition of the retest necessity is completed for all the sample tubes T of the preceding rack L1 after the supply of the washing fluid tube C of the following rack L2 is suspended, the washing fluid tube C of the following rack L2 is automatically supplied to the measurement units 31, 32, which alleviates the trouble of the user.

According to the present embodiment, after executing the washing, the measurement units 31, 32 are automatically shut down and the information processing unit 4 is automatically shut down, so that the user can omit the operation of waiting for the washing process that takes a long time and then manually shutting down the power of the device. The trouble of the user thus can be alleviated.

According to the present embodiment, in a configuration having two or more measurement units, if the retest necessity acquisition is completed for all samples in the preceding rack L1 and some of the samples are determined to be necessary to be retested, the washing is started for only one measurement unit while the other measurement unit performs the aspiration for retest. Therefore, a time consumed for washing all measurement units can be minimized.

The embodiment of the present invention has been described above, but the embodiment of the present invention is not limited thereto.

For instance, the blood cell counting apparatus has been illustrated as the measurement unit in the embodiment described above, but the measurement unit may be a urine analyzer or an immunology analyzer measuring a serum.

In the embodiment described above, the sample analyzer 1 in which the sample is aspirated by the piercing pipette 31d, 32d after the sample tube T is interiorly retrieved by the hand portions 31a, 32a of the measurement units 31, 32 has been illustrated, but the present invention may be applied to a sample analyzer in which the piercing pipette is arranged at the retrieving positions P31a, P32a and the sample of the sample tube T is aspirated in a state where the sample tube T is held on the rack without interiorly retrieving the sample tube T.

In the embodiment described above, the rack transporting portion 23 is controlled to position the washing fluid tube C at the feeding position P1 without positioning at the retrieving positions P31a, P32a of the measurement units 31, 32 so that the supply of the washing fluid to the measurement units 31, 32 is suspended, but the present invention is not limited to this embodiment. Alternatively, the rack transporting portion 23 may be configured to position the washing tubes C at the retrieving positions P31a, P32a, and the measurement units 31, 32 may be configured to avoid retrieving inside the washing fluid tube C of the holder of the rack L to suspend the supply of the washing fluid. Or the measurement unit 31, 32 may be configured to control the hand portions 31a, 32a not to position the washing fluid tube C at the aspirating positions P31c, P32c in order to suspend the supply of the washing fluid. Or the measurement unit may be configured to control the piercing pipette 31d, 32d not to aspirate washing fluid in the washing fluid tube C for the same purpose.

In the embodiment described above, the supplying order of the tube is determined by identifying the type of tube held in the rack L in order by the barcode unit B2, but the barcode may not be used. For instance, the information processing unit 4 may accept the measurement reservation of the sample and the washing reservation using the washing fluid, and the measurement units 31, 32 may be configured to execute the reserved operation accepted by the information processing unit 4 in the order specified by the user. In this case, the supplying order of the tube is determined based on the specified order of the reserved operation.

In the embodiment described above, the barcode given to the tube is read on the rack transporting portion 23 connecting the right table 21 and the left table 22, but the present invention is not limited thereto. For instance, the transport apparatus for supplying the rack L to the right table 21 may be connected to the upstream of the transportation unit 2, and a barcode reader may be provided in a path between the transport apparatus and the right table 21.

In the embodiment described above, a mode of reading the barcode while transporting the rack L is shown, but a mode of including a hand held type barcode reader may be adopted. In such a mode, the barcodes of a plurality of tubes are read with the barcode reader in advance, and the tubes are arranged on the rack L in an order of reading the barcode.

Figure 14:
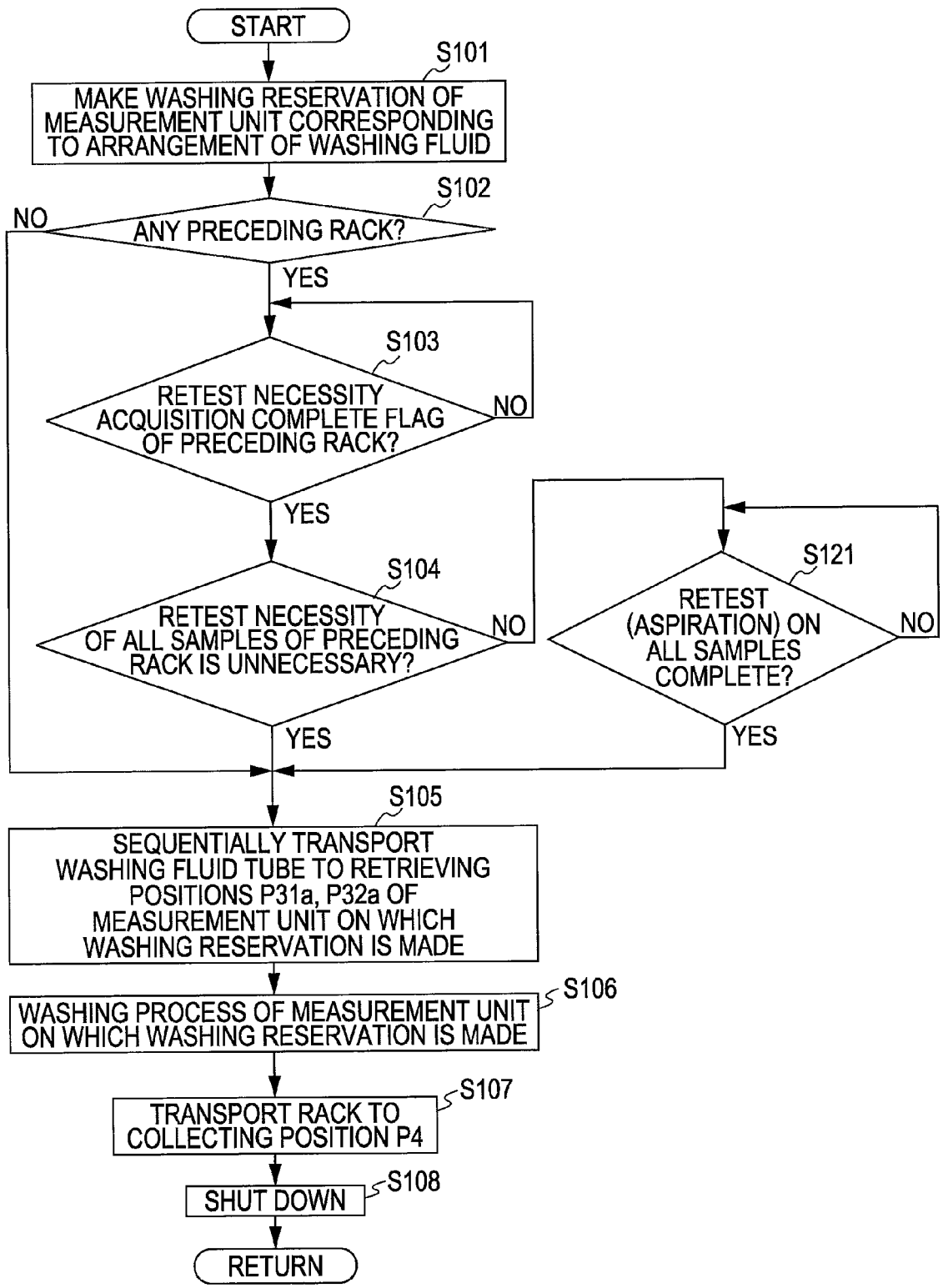
FIG. 14 is a view showing a flowchart of a transportation control of a rack for performing a washing and a shutdown according to the modified embodiment 1.

In the embodiment described above, in the configuration including two measurement units 31, 32, if the retest is necessary for the sample of the preceding rack L1, the washing fluid tube C is supplied only to the measurement unit 32 on the upstream side before the aspiration for the retest of all the samples is completed, but the supply of the washing fluid tube C to all the measurement units 31, 32 may be suspended until the aspiration for the retest is completed for all the samples of the preceding rack L1. In this case, the flowchart of FIG. 10 is modified to modified embodiment 1 in FIG. 14. In other words, if there is a sample that needs retest in the preceding rack L1 in S104 (S104: NO), the CPU 401 suspends the supply of the washing fluid to the measurement unit until the aspiration for the retest with respect to all the samples that need the retest is completed (S121). After the aspiration for all the retests is completed (S121: YES), the CPU 401 executes washing on the measurement unit to be washed (S105 to S108).

Figure 15:
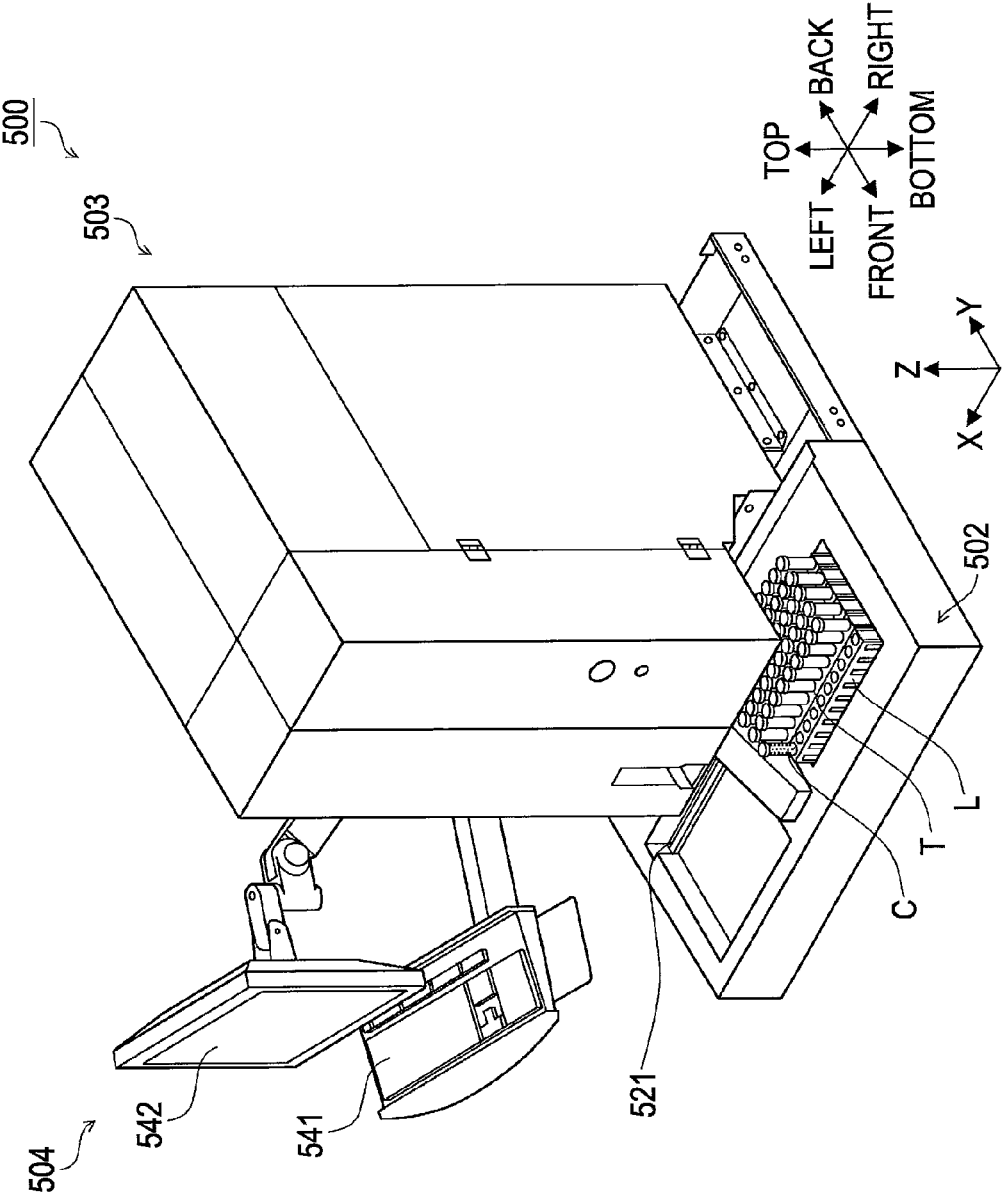
FIG. 15 is a view showing an external appearance of a sample analyzer according to the modified embodiment 2.

In the embodiment described above, the sample analyzer 1 including two measurement units 31, 32 is illustrated, but three or more measurement units may be arranged and a smear preparing apparatus may be additionally arranged. As shown in modified embodiment 2 of FIG. 15, a sample analyzer 500 including one measurement unit 503 may be adopted. In this case, a transportation unit 502 has a rack transporting portion 521 configured shorter than in the embodiment described above, but an information processing unit 504 and other configurations are configured similar to the above.

Figure 16A:
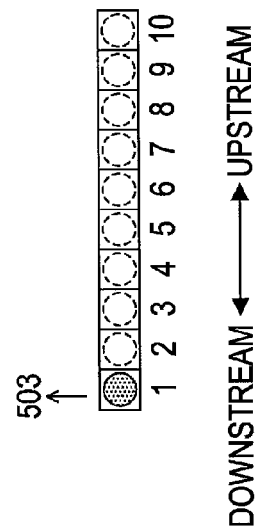
FIG. 16A is a view showing an arrangement rule of a washing fluid tube according to the modified embodiment 2.

FIG. 16A is a view showing an arrangement rule of the rack L of the washing fluid tube C in the case of modified embodiment 2. The washing fluid tube C is installed at the holding position 1 positioned on the most downstream side in the transporting direction.

Figure 16B:
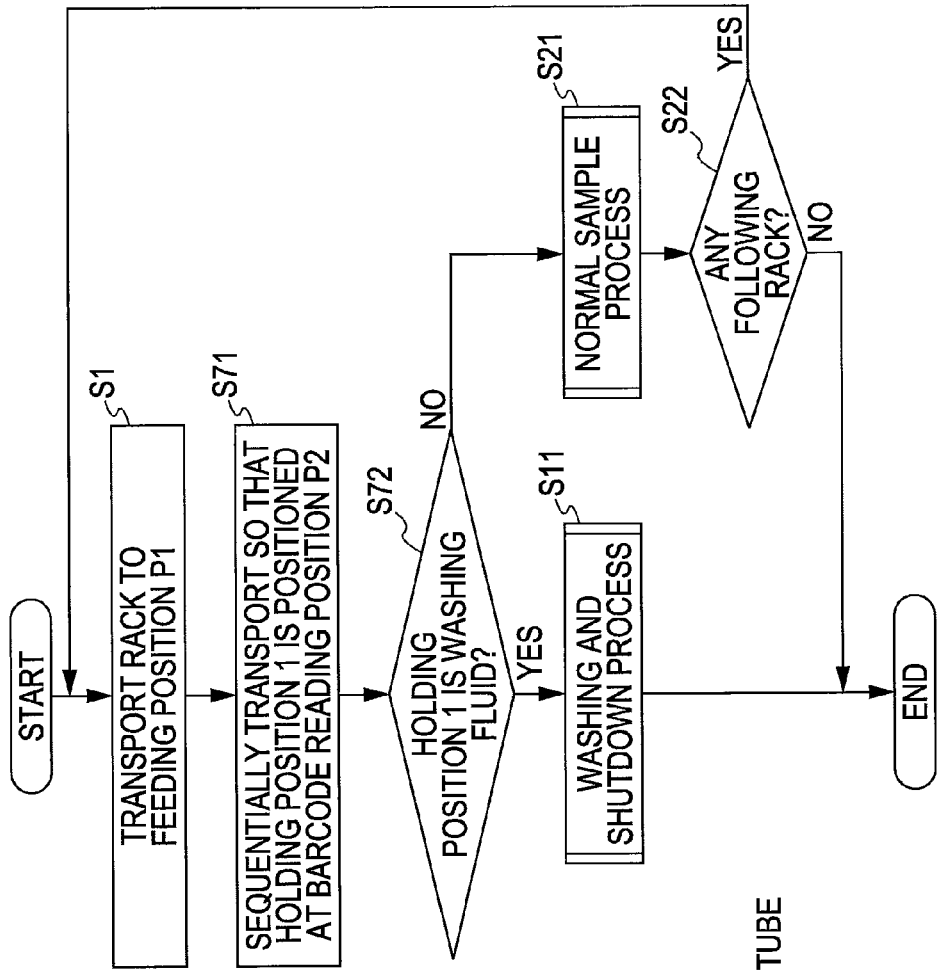
FIG. 16B is a view showing a flowchart of transportation of a rack according to the modified embodiment 2.

FIG. 16B is a flowchart showing a flow of the control operation of the rack L in the case of modified embodiment 2. The processes similar to the embodiment described above shown in FIG. 9 are denoted with similar reference numerals, and the detailed description will be omitted.

In the case of modified embodiment 2, which one of the washing and shutdown process or the sample process to be performed is determined according to the type of tube arranged at the holding position 1.

When the rack L is transported to the feeding position P1 (S1), the CPU 401 operates the rack transporting portion 23 to transport the same so that the holding position 1 of the rack L is positioned at the barcode reading position P2 (S71). The barcode information of the tube installed at the holding position 1 is then read by the barcode unit B2, and whether the washing fluid tube C is installed at the holding position 1 is determined (S72). If the washing fluid tube C is installed at the holding position 1 (S72: YES), the CPU 401 initiates the washing and shutdown process (S11). If the washing fluid tube C is not installed at the holding position 1 (S72: NO), the CPU 401 executes the normal sample process (S21). In this case, the washing and shutdown process is carried out according to the flowchart shown in FIG. 14. In other words, the washing operation by the washing fluid tube C held in the following rack L is suspended until the aspiration for the retest is completed for all the sample tubes T held in the preceding rack L. The following holding position determination steps S201, S202 in the normal sample process S21 are modified to include the holding position 2, so that the holding positions 2 to 10 are the target of determination.

In modified embodiment 2, therefore, effects similar to the embodiment described above are obtained even with the configuration including one measurement unit.

In the embodiment described above, the rack L includes holders for ten tubes, but the number of holders may be other numbers. The arrangement rule of the washing fluid tube C is to be arranged on the most downstream in the transporting direction of the rack L, but may be positioned on the most upstream or may be positioned at other positions. Furthermore, the arrangement rule of the washing fluid tube C on the rack L may not be defined.

In the embodiment described above, the supply of the washing fluid tube C accommodated in the following rack L2 to the measurement units 31, 32 is suspended when the sample tube T is held in the preceding rack L1 and the washing fluid tube C is held in the following rack L2. However the supply of the washing fluid tube C to the measurement units 31, 32 may be suspended when both of the washing fluid tube C and the sample tube T is installed to the same rack L.

Figure 16C:
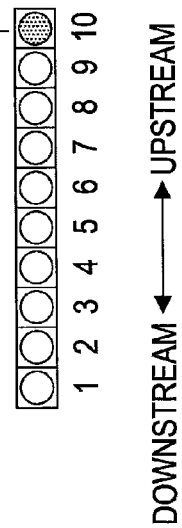
FIG. 16C is a view showing an arrangement rule of a washing fluid tube according to the modified embodiment 3.

As shown in modified embodiment 3 of FIG. 16C, in the case of the rule in which the washing fluid tube C is arranged at the holding position 10, whether the sample tube T is installed at any of the holding positions 1 to 9 is determined. If the sample tube T is installed, the supply of the washing fluid tube C to the measurement units 31, 32 is suspended until the aspiration for the retest of the sample tubes T at the holding positions 1 to 9 is completed.

Figure 17:
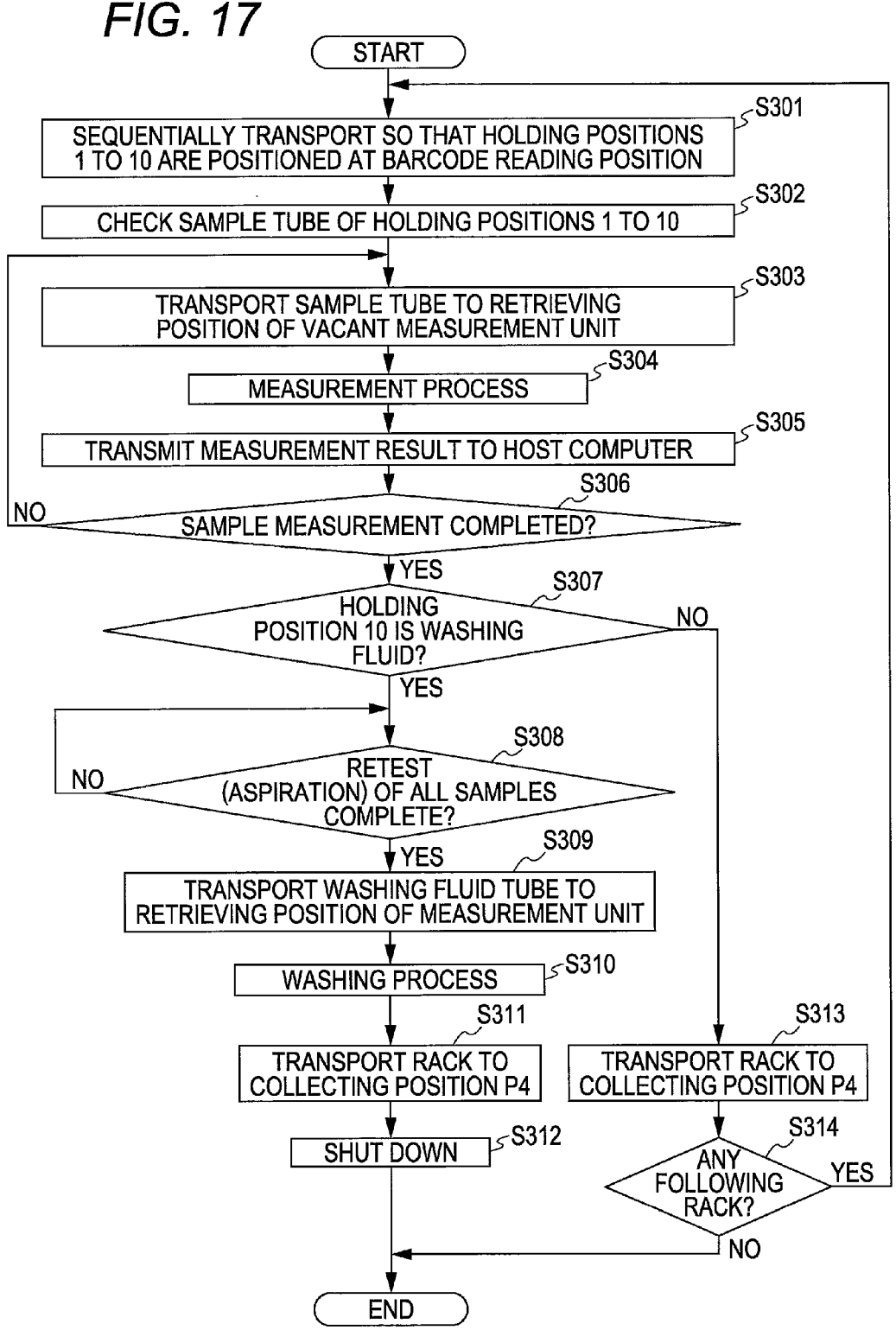
FIG. 17 is a view showing a flowchart of transportation of a rack according to the modified embodiment 3.

FIG. 17 is a flowchart showing a flow of the control operation of the rack L in the case of modified embodiment 3.

With reference to FIG. 17, the CPU 401 performs the barcode reading of the tube installed in the holder of the rack L, and the measurement process as well as the retest process of the sample tube T installed in the rack L, (S301 to S306), similar to the embodiment described above. When the measurement is completed for all the sample tubes T accommodated in the rack L (S306: YES), the CPU 401 determines whether or not the washing fluid tube C is at the holding position 10 (S307).

If the washing fluid tube C is not at the holding position 10 (S307: NO), the CPU 401 operates the rack transporting portion 23 to transport the rack L to the collecting position P4 (S313). The CPU 401 then determines whether there is a following rack L (S314), and the processing of the following rack L is performed. If the washing fluid tube C is at the holding position 10 (S307: YES), the CPU 401 determines whether or not the aspiration for the retest is completed for all the samples of the rack L (S308). If the aspiration for the retest is not completed (S308: NO), the CPU 401 waits for the following processing until the aspiration for the retest is completed. If the aspiration for the retest is completed (S308: YES) for all the samples of the rack L, the CPU 401 supplies the washing fluid tube C at the holding position 10 to the measurement unit, and performs the washing process and the shutdown (S309 to S312). Such processes are similar to S105 to S108 of FIG. 10, and thus the detailed description will be omitted.

In the case of modified embodiment 3, when the washing fluid tube C follows the sample tube T of the same rack L, the supply of the following washing fluid tube C to the measurement unit is suspended, and thus the washing is avoided from being automatically starting. Therefore, the retest can be smoothly carried out for all the sample tubes T of the preceding rack.

Figure 18:
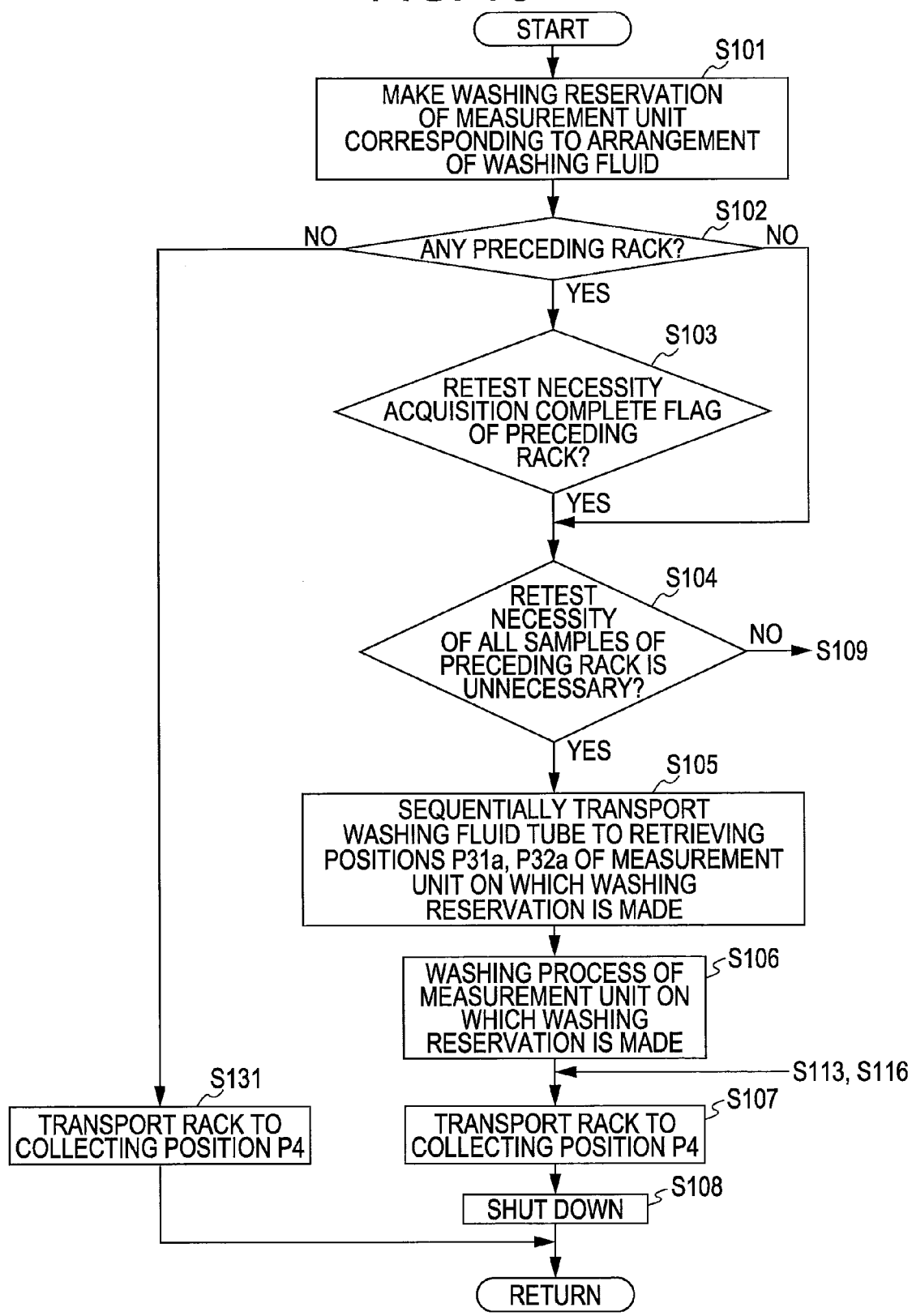
FIG. 18 is a view showing a flowchart of transportation of a rack for performing a washing and a shutdown according to the modified embodiment 4.

In the embodiment described above, if the following rack L2 is identified as holding the washing fluid tube C, the supply of the washing fluid tube C of the following rack L2 to the measurement units 31, 32 is suspended until the acquisition of the retest necessity is completed or until the aspiration for the retest is completed if the acquisition of the retest necessity is not completed for all the samples of the preceding rack L1, but the supply of the washing fluid tube C to the measurement units 31, 32 may be skipped, as shown in modified embodiment 4 of FIG. 18.

With reference to FIG. 18, in the case of modified embodiment 4, if the retest necessity acquisition complete flag for all the samples of the preceding rack L1 is not set (S103: NO) after determining that the following rack L2 includes the washing fluid tube C, the CPU 401 operates the rack transporting portion 23 to transport the following rack L2 to the collecting position P4 (S131). The following rack L2 transported to the collecting position P4 is discharged to the left table 22 by a rack pushing mechanism 23a. The supply of the washing fluid tube C to the measurement units 31, 32 is skipped in such manner, and the process with respect to the following rack L2 is completed.

FIG. 19 is a view showing an example of the operation state of the rack transporting portion 23 of the preceding rack L1 and the following rack L2 in the case of modified embodiment 4.

FIG. 19A shows a state similar to FIG. 12B, and FIG. 19B shows a state similar to FIG. 12C, and thus the description will be omitted.

FIG. 19C is a view showing a state of when the following rack L2 is collected to the left table 22 while waiting for the retest necessity acquisition of the preceding rack L1. Such state corresponds to a state in which the CPU 401 is processing the completion waiting process of the aspiration for the retest of S207 of FIG. 11A, the retest process of FIG. 11B, and the flag setting process of FIG. 11C in parallel for the preceding rack L1 and processing the transportation to the collecting position P4 of S131 of FIG. 18 for the following rack L2. The preceding rack L1 has the measurement process of the sample tube T of all the holders at the holding positions 1 to 10 completed and waits in the transportation space P5 of the rack transporting portion 23. In this case, the preceding rack L1 is determined that the retest necessity is already acquired and the retest is unnecessary for the sample tubes T at the holding positions 1 to 9. The determination result on the necessity of retest is not yet acquired for the sample tube T at the holding position 10 of the preceding rack L1. The following rack L2 skips the supply of the washing fluid tube C to the measurement units 31, 32 and is collected to the left table 22 since the retest necessity acquisition of the preceding rack L1 is not completed when identified as including the washing fluid tube C.

FIG. 19D is a view showing a state of when the retest necessity is acquired for the sample tubes T of all the holders of the preceding rack L1. Such state corresponds to a state in which the retest process of FIG. 11B and the flag setting process of FIG. 11C are completed, and the CPU 401 is processing S208 of FIG. 11A for the preceding rack L1 and completed with processing for the following rack L2. The preceding rack L1 is determined that the retest necessity is already acquired and the retest is unnecessary for the sample tubes T of all the holders at the holding positions 1 to 10. Thus, the preceding rack L1 is pushed away to the left table 22.

Therefore, if identified that the holder of the following rack L2 includes the washing fluid tube C by the barcode unit B2, the supply of the washing fluid tube C of the following rack L2 to the measurement units 31, 32 is skipped if the retest necessity acquisition of all the samples of the preceding rack L1 is not completed.

In the case of modified embodiment 4 as well, if the following rack L2 in which the washing fluid tube C is installed follows the preceding rack L1 in which the sample tube T is installed, the supply of the washing fluid tube C of the following rack L2 is skipped and thus the washing is avoided from being automatically started, similar to the embodiment described above. Therefore, the retest can be smoothly carried out for all the sample tubes T of the preceding rack L1.

In the embodiment described above, the following rack L2 is evacuated to the feeding position P1 and waited thereat until the acquisition of the retest necessity of the sample tube T of the preceding rack L1 is completed, but may be waited at other positions on the rack transporting portion 23. The following rack L2 may be evacuated as needed with the transportation of the preceding rack L1 without waiting at a predetermined position.

In the embodiment described above, the sample tube T and the washing fluid tube C are installed in the rack L and supplied to the measurement units 31, 32, but may not be installed in the rack L, and the sample tube T and the washing fluid tube C may be directly installed in the rack transporting portion 23 one at a time and transported to be supplied to the measurement units 31, 32.

Furthermore, in the embodiment described above, the presence or absence of the tube, and the type of sample tube T and washing fluid tube C is identified by the barcode unit B2, but may be identified with other identification means. For instance, an IC chip indicating the sample ID and the washing fluid ID may be arranged on the tube, and an IC chip reader may be used or an optical sensor for identifying the shape may be used with the shape of the tube differed between the sample and the washing fluid. A two-dimensional code arranged with dots such as the QR code (registered trademark) may be used in place of the linear barcode.

In the embodiment described above, the measurement units 31, 32 and the information processing unit 4 automatically perform shut down after executing the washing, but may be restart rather than the shutdown, where the user may set whether to perform the shutdown or perform the restart according to the application of the information processing unit 4.

In the embodiment described above, the necessity of the retest is determined by the host computer 5, and the determination result of the retest necessity is acquired by the information processing unit 4, but the necessity of the retest may be determined by the information processing unit 4.

In the embodiment described above, the measurement units 31, 32 respectively perform the measurement of the sample and the process of the retest, but the measurement unit 32 on the upstream side may perform only the process of the sample measurement, and the measurement unit 31 on the downstream side may perform only the process of the retest.

Furthermore, in the embodiment described above, whether the rack L performs the sample process or performs the washing and shutdown process is determined by identifying the sample ID and the washing fluid ID of the holding positions 1, 2 of the rack L, but determination may be made whether to perform the sample process or whether to perform the washing and shutdown process by the rack ID.

The embodiment of the present invention may be appropriately modified within a scope of the technical idea described in the Claims.

What is claimed is:

1. A sample analyzer comprising:
a measurement section that aspirates samples in sample tubes and measures the aspirated samples;
a transportation section that transports a plurality of tubes to supply the tubes to the measurement section;
an identification section that obtains identification data of the tubes transported by the transportation section; and
a system controller coupled to the measurement section, the transportation section and the identification section and controlling operations of the measurement section, the transportation section and the identification section;
wherein the system controller is programmed to perform operations comprising:
performing analysis based on a measurement result performed by the measurement section;
receiving a determination result regarding whether an aspirated sample by the measurement section needs a re-measurement, the determination result being made based on the measurement result of the aspirated sample and the determination result comprising a first determination result that a re-measurement is needed for the aspirated sample and a second determination result that no re-measurement is needed for the aspirated sample;
when recognizing a presence of a washing fluid tube transported by the transportation section based on the identification data obtained by the identification section, controlling the transportation section to supply the washing fluid tube to the measuring section, and controlling the measurement section to aspirate the washing fluid from the washing fluid tube whereby an aspirated washing fluid is used to wash at least one part of the measurement section; and
when recognizing a presence of the washing fluid tube transported by the transportation section prior to receipt of the determination result regarding whether a re-measurement is needed or not for the already aspirated sample, prohibiting the supply of the washing fluid in the washing fluid tube to the measurement section.

2. The sample analyzer according to claim 1, wherein the system controller is further programmed to perform removing the prohibition of the supply of the washing fluid to the measurement section upon receipt of the second determination result.

3. The sample analyzer according to claim 1, wherein upon receipt of the first determination result, the system controller is further programmed to perform controlling the transportation section to supply the sample tube to the measurement section and then controlling the measurement section to aspirate the sample again, performing a re-measurement on a newly aspirated sample, and removing the prohibition of the supply of the washing fluid to the measurement section after the aspiration of the sample for the re-measurement is completed.

4. The sample analyzer according to claim 1, wherein the transportation section includes a transportation path extending from a first position to a second position, and operates to position a tube at a tube supplying position between the first position and the second position by transporting the tube along the transportation path.

5. The sample analyzer according to claim 4, wherein when continuously supplying the sample tubes comprising a first sample tube and a second sample tube to the measurement section, the system controller is further programmed to perform controlling the transportation section to:
   transport the first sample tube to the tube supplying position;
   move the first sample tube from the tube supplying position to a different place after aspiration of the sample in the first sample tube is completed; and
   transport the second sample tube to the tube supplying position without waiting to receive the determination result for the sample in the first sample tube.

6. The sample analyzer according to claim 1, wherein the transportation section transports a rack for holding a group of the plurality of tubes.

7. The sample analyzer according to claim 1, wherein the system controller is further programmed to control the measurement section to automatically shut down after performing washing with the washing fluid in the washing fluid tube supplied to the measurement section.

8. A sample analyzer comprising:
   a measurement section that aspirates samples in sample tubes and measures aspirated samples,
   a transportation section that transports a plurality of tubes to supply the tubes to the measurement section; and
   a system controller coupled to the measurement section and the transportation section and controlling operations of the measurement section and the transportation section,
   wherein the system controller:
   acquires a determination result regarding whether an aspirated sample by the measurement section needs a re-measurement, the determination result being made based on a result of measurement on the aspirated sample; and
   controls the measurement section to aspirate a washing fluid in a washing fluid tube and then use an aspirated washing fluid to wash at least one part of the measurement section if the washing fluid tube is supplied by the transportation section; and
   wherein when a preceding sample tube is supplied to the measurement section, followed by a subsequent washing tube, the system controller is programmed to control the transportation section to suspend supply of washing fluid in the subsequent washing fluid tube to the measurement section until the system controller completes acquisition of the determination result regarding whether an aspirated sample from the preceding sample tube needs a re-measurement.

9. The sample analyzer according to claim 8, wherein upon acquisition of the determination result indicating the aspirated sample from the preceding sample tube does not need a re-measurement, the system controller is further programmed to control the transportation section to supply the washing fluid tube to the measurement section, and control the measurement section to execute aspiration of the washing fluid from the subsequent washing fluid tube and a washing process with an aspirated washing fluid.

10. The sample analyzer according to claim 8, wherein the transportation section includes a transportation path extending from a first position to a second position, and operates to position a tube at a tube supplying position between the first position and the second position by transporting the tube along the transportation path.

11. The sample analyzer according to claim 10, wherein when continuously supplying the sample tubes comprising a first sample tube and a second sample tube to the measurement section, the system controller is further programmed to control the transportation section to:
   transport the first sample tube to the tube supplying position,
   move the first sample tube from the tube supplying position to a different place, and
   transport the second sample tube to the tube supplying position without waiting for acquisition of the determination result for the first sample tube.

12. The sample analyzer according to claim 11, wherein the system controller is further programmed to control the transportation section to transport the first sample tube again to the tube supplying position upon acquisition of the determination result that the sample from the first sample tube needs a re-measurement.

13. The sample analyzer according to claim 8, wherein the system controller is further programmed to control the transportation section to supply the subsequent washing fluid tube to the measurement section, and control the measurement section to execute aspiration of the washing fluid from the subsequent washing fluid tube and a washing process with the aspirated washing fluid after the aspiration for the re-measurement of the sample tube is completed.

14. The sample analyzer according to claim 8, further comprising an identification data unit for obtaining identification data for identifying a type of tube; wherein the system controller identifies the type of tube transported by the transportation section using the identification data obtained by the identification data unit, and determines whether a washing fluid tube follows a sample tube.

15. The sample analyzer according to claim 8, wherein the system controller is further programmed to control the transportation section to stop a following rack for holding one group of the plurality of tubes at a predetermined position until each sample tube held in a preceding rack for holding another group of the plurality of tubes is tested to determine whether a re-measurement is needed for each sample tube, when a washing fluid tube for containing a washing fluid is held in the following rack.

16. The sample analyzer according to claim 8, wherein the transportation section includes a transporting portion for transporting a rack from upstream towards downstream, and the predetermined position is a most upstream position or a most downstream position.

17. The sample analyzer according to claim 8, wherein the washing process takes longer than aspiration and measurement of the sample from the preceding sample tube and acquisition of the determination result whether or not the sample from the preceding sample tube requires a re-measurement.

* * * * *